(12) United States Patent
Albeck-Marom

(10) Patent No.: US 7,919,324 B2
(45) Date of Patent: *Apr. 5, 2011

(54) LIQUID TESTER

(75) Inventor: Orit Albeck-Marom, Udim (IL)

(73) Assignee: Orit Marom-Albeck, Udim (IL)

( * ) Notice: Subject to any disclaimer, the term of this patent is extended or adjusted under 35 U.S.C. 154(b) by 548 days.

This patent is subject to a terminal disclaimer.

(21) Appl. No.: 11/954,304

(22) Filed: Dec. 12, 2007

(65) Prior Publication Data

US 2008/0227216 A1    Sep. 18, 2008

Related U.S. Application Data

(63) Continuation-in-part of application No. 10/145,797, filed on May 14, 2002, now Pat. No. 7,319,037.

(51) Int. Cl.
*G01N 33/18* (2006.01)

(52) U.S. Cl. .......... 436/39; 436/163; 422/401; 422/402; 422/430

(58) Field of Classification Search ............ 436/39, 436/163; 422/58, 61, 401, 402, 430
See application file for complete search history.

(56) References Cited

U.S. PATENT DOCUMENTS 4,126,417 A * 11/1978 Edwards .................. 422/56
4,409,182 A * 10/1983 Macklem ................. 422/61

* cited by examiner

*Primary Examiner* — Lyle A Alexander

(74) *Attorney, Agent, or Firm* — Edward Langer, Adv.; Law Office of Edward Langer

(57) ABSTRACT

A liquid testing device for determining the value of at least one property of a liquid. The liquid testing device includes a planar base and at least one test section, located on the planar base, with a reference color section located adjacent to the test section, which exhibits a color according to the value, as a result of reaction of a reagent with the liquid. The reference color section includes a plurality of different reference colors arranged for easy visual color comparison with the test result. The reference color section is placed adjacent to and in contact with the test section, with the test section having sufficient length so that it substantially encompasses the entire reference color section with its plurality of different reference colors. Thus, when the test section exhibits a reaction color, the visual comparison is simplified since the reference color which matches the reaction color becomes substantially visually merged and self-aligned therewith.

34 Claims, 12 Drawing Sheets

LIQUID TESTER

The present application is a Continuation-in-Part of U.S. patent application Ser. No. 10/145,797 filed May 14, 2002 now U.S. Pat. No. 7,319,037 by the Applicant, the disclosure of which is hereby incorporated by reference.

FIELD OF THE DISCLOSED TECHNIQUE

The disclosed technique relates to methods and systems for testing liquids in general, and to methods and systems for testing water, in particular.

BACKGROUND OF THE DISCLOSED TECHNIQUE

Systems and methods for testing water for chemicals and other properties are known in the art. A prevalent method consists of inserting into the tested water an absorbent material, such as paper, which is impregnated with a chemical reagent. The reagent chemical is designed to react with predetermined chemicals or predetermined liquid properties. As a result of this reaction, the color of the reagent chemical changes, and this is visible on the absorbent material. Accordingly, a color change is achieved when the water under test contains these predetermined chemicals or is characterized by the predetermined liquid properties. The hue of the resulting color can further quantitatively determine the level of the detected chemical or property, by comparing the hue with a standard color scale.

The visual comparison of the resulting color change with the standard color scale is a critical part of this test procedure, and the exactness of this color comparison is vital to achieving an accurate test result. With the large variation in colors which may result from the test, it becomes exceedingly difficult to make this visual comparison. One of the shortcomings of the available test kits is the lack of a mechanism to simplify and improve the visual comparison. The prior art systems are now reviewed, and it becomes clear that they lack a simplified approach to this visual color comparison U.S. Pat. No. 3,876,378 to Montagnon, entitled "Analytic Device Utilizing Reaction-Sensitive Chemical Product", is directed to an apparatus for chemical testing of liquids using a chemical reagent. The construction of this apparatus is intended to overcome some of the problems that may occur in such tests. The apparatus includes a vessel with a flange at its bottom forming a groove, and a disc made of absorbent material, which comfortably fits inside the groove. The disc is impregnated with a chemical reagent, so that upon introduction of the tested liquid, the disc may undergo a color change, depending on the conditions of the liquid.

U.S. Pat. No. 4,904,605 entitled "Method and Apparatus for Residential Water Test Kit" issued to O'Brien et al., is directed to a system and method for testing water for a plurality of chemicals and other characteristics. The water test kit includes a container with a label on the exterior. The label includes a color comparison chart and optionally, operating instructions. The color comparison chart indicates the properties to be tested. Each row of the chart pertains to one chemical or property, and includes a scale of colors and their corresponding levels of the chemical concentration or the property. The kit further includes a dipstick or test strip. The dipstick or test strip is divided into a plurality of areas. Each area contains a reagent that reacts to a specific chemical or liquid property, producing a color change in that area. To test the water using this device, the user first fills the bottle with tap water. He (or she) then fully immerses the test strip in the sample bottle and waits for 30 seconds. Next, he (or she) removes the test strip from the water, and positions the test strip so that it is aligned with the color chart. Finally, he (or she) compares the color of each of the test strip areas to the corresponding section of the chart.

Numbers indicating problematic levels are underlined and may also be printed in a different color (e.g., red) from the rest of the numbers on the chart. A solution chart may also be provided, on which recommendations are given to solve the problems with water, possibly by reference to different water filters and the like. The need for the strip to be matched with the color chart makes this system relatively complicated to operate, and may result in misreadings or other errors by the unskilled user. It is also necessary for all of the separate parts of the kit to be present in order for the testing to be possible.

A disadvantage of this type of testing device is that once the strip has been immersed in water and removed from it, placement of the strip in alignment with the color chart is a messy process, since the excess water drips onto the color chart. The procedure is unpleasant to perform, and is certainly not aesthetic, especially if the liquid being tested has an odor, such as in the case of a urine sample.

Another method for colorimetric testing of water known in the art consists of inserting a reagent into the water sample and allowing it to react inside the water, thus causing the water to change color, and then comparing the color of the water with a standard color scale.

U.S. Pat. No. 3,381,572 entitled "Colorimetric Testing Device" issued to Tuwiner, is directed to a device for quantitatively determining the concentration of a chemical or the levels of a property such as pH. The apparatus includes an optical color index unit, adjacent to a container for the tested sample. The index unit color changes gradually from one end to another, in correspondence with the color change of the tested sample at different levels of the property being tested. The index unit also has numbers printed thereon to indicate the corresponding levels. To perform the test, the user inserts the sample, together with a color-indicating reagent, into the container and compares the changed color of the sample with the index unit color scale.

U.S. Pat. No. 4,125,376 entitled "Method for Detecting Water Pollutants" issued to Razulis, is directed to a method for identifying chemicals in water. The apparatus is a transparent container, with an urethane foam cube disposed therein, and a plug for scaling the tube. The urethane foam cube is impregnated with a specific spot detection chemical. The chemical produces a calorimetric indication when exposed to specific pollutants in the tested water sample. The method is carried out by adding the water to the container, sealing the container with a plug and then shaking it. The color change is then compared to a color comparator chart of the specific pollutants.

U.S. Pat. No. 4,180,009 issued to Voss et al., and entitled "Ion Concentration Testing Apparatus", is directed to a device for determining different ion concentrations in swimming pool water. The device includes two measurement containers, a reference container and an indicating screen. The measurement containers and the reference container are bounded on one side by a common wall. The indicating screen is located in front of the common wall and includes a plurality of indicating windows associated with the measurement containers and a plurality of indicating windows associated with the reference container. The measurement containers and the reference container are arranged in a row and each has a square or a rectangular cross section. The indicating windows are distributed over the height of the measurement containers and the reference container. Each of the indicating windows associated with the reference container, has a reference or standard coloration corresponding to a predetermined ion concentration. The indicating windows are transparent.

The indicating screen further includes a plurality of marks adjacent to the indicating windows associated with the measurement containers. The value of each of the marks is related with the respective indicating window associated with the reference container. The user fills the measurement containers with water and inserts different color forming reagents, according to the particular ion concentration to be tested, in each measurement container. The color forming reagents dissolve and the water in each measurement container acquires a color which corresponds with the concentration of the ion. The user compares the color of the water seen through the indicating windows associated with a measurement container, with the respective reference coloration of the indicating window associated with the reference container. The user determines the ion concentration by reading the value of the mark, which corresponds with the reference coloration which was identified as a result of this comparison.

Merck KGaA located in Darmstadt, Germany, discloses a first method for determining the concentration of substances in water, landfills and soil. According to the first method, the user adds a liquid reagent to a liquid sample, thereby rendering a color to the liquid. The concentration of the substance is measured by a photometer, according to the color of the liquid. Merck KGaA discloses a second method for testing a solution. According to the second method, the user dips a test strip in the solution. After a given reaction time has elapsed, the user compares the color of the reaction zone with a color scale on the package, thereby determining the concentration.

Merck KGaA discloses a system for determining the concentration of substances or a parameter in a liquid. The system includes an electronic instrument, a plurality of test strips and a bar code. Each of the test strips are designated to test the concentration of a selected substance or a selected parameter in the liquid. The bar code includes information respective of the selected substance or the selected parameter. The user calibrates the electronic instrument, by passing the bar code through the electronic instrument. The user then dips a test strip in the liquid, whereby the reaction renders a color to the test strip. The user passes the test strip through the electronic instrument, the electronic instrument determines the value of the concentration or the parameter and displays this value on a display.

Hach Company located in Colorado, U.S.A., discloses a calorimetric method for determining the concentration of a parameter in a sample. The user adds a reagent to the sample, thereby rendering a color to the sample. The user determines the concentration by comparing the color of the sample with test strips, color cubes, color discs, a calorimeter or a spectrometer. Hach discloses an electrochemical method for determining the concentration of a parameter. According to the electrochemical method, the presence or the absence of a parameter is determined, by measuring the electrical activity of a sample. Hach discloses a titration method for determining the concentration of a substance. According to the titration method, the user dispenses a reagent on the sample, until the color of the sample changes. The user determines the concentration by measuring the volume of the reagent, which is dispensed (e.g., by counting the drops of the reagent dispensed from an eye dropper, or according to the reading of a digital titrator).

Other variations of performing the test include determining the concentration of parameters in liquid samples, by using a chemical indicator which changes its color when it reacts with a reagent in a liquid. This technique is used in testing methods including calorimetric and photometric methods using drop tests, and calorimetric and photometric methods using powder pillows and test strips.

In a research project in which the inventor participated, the goal was to test the water quality in a local area. For this purpose, integrated water testing kits were used for testing the water in multiple randomly selected private homes. Testing the tap water in each and every one of the selected homes was a complicated and exceedingly long test procedure, as it required mixing the reagents, comparing the resulting colors with separate color charts, and repeating the entire test multiple times for other parameters.

Additionally, those tests, which utilized test strips, were quite tough to interpret due to the difficulty associated with distinguishing between two close colors. On top of that, the resulting colors did not always remain stable, and so, comparing the resulting colors against the color charts was quite difficult. As a result, there were times that the entire test had to be repeated, since in a sequence of tests, the resulting colors might have faded before they could be compared with the color charts.

Typically, the entire procedure of testing the tap water in a single home took approximately one hour. Therefore, an aim of the present invention is to design a simplified testing device, which eliminates long and complicated testing procedures.

SUMMARY OF THE DISCLOSED TECHNIQUE

It is an object of the disclosed technique to provide a novel method and system for determining the properties of a liquid.

The present invention overcomes the disadvantages of prior art testing procedures by providing a liquid testing device that enables simultaneous testing of several parameters in relatively short time (i.e., several minutes). In addition, the inventive testing device simplifies the visual comparison of the color change against the reference color charts and reduces the probability of introducing errors when reading and interpreting the results.

In accordance with the disclosed technique, there is thus provided a liquid testing device for determining the value of at least one property of a liquid. The liquid testing device includes a planar base and at least one test section, located on the planar base. The at least one test section includes a test sub-section and a reference color section located adjacent to the test sub-section. The at least one test sub-section exhibits a color according to the value, as a result of reaction of a reagent with the liquid. The reference color section includes a plurality of different reference colors arranged for easy visual color comparison with the test result. The inventive testing device places the reference color section adjacent to and in contact with the test section, with the test section being of sufficient length so that it substantially encompasses the entire reference color section with its plurality of different reference colors. Thus, when the test section exhibits a reaction color, the visual comparison is simplified since the reference color which matches the reaction color becomes substantially visually merged and self-aligned therewith.

In accordance with another aspect of the disclosed technique, there is thus provided a liquid testing device for determining the value of each of a plurality of properties of a liquid. The liquid testing device includes a container, a plurality of test sections and a plurality of reference sections. Each container has at least one transparent portion. Each of the test sections exhibits a color according to the value, as a result of reaction of a reagent with the liquid. Each of the reference color sections is located adjacent to a respective one of the test sections and each of the reference sections includes a plurality of different reference colors.

In accordance with a further aspect of the disclosed technique, there is thus provided a liquid testing device for determining the value of each of a plurality of properties of a liquid. The liquid testing device includes a plurality of containers, a test section for each of the containers and a reference color section for each of the test sections. Each container has at least one transparent portion. Each test section exhibits a color according to the value, as a result of reaction of a reagent with the liquid. Each reference section is located adjacent to a respective test section, wherein the reference color section includes a plurality of different reference colors.

In accordance with another aspect of the disclosed technique, there is thus provided a method for determining the value of a plurality of properties of a liquid. The method includes the procedures of providing a plurality of test sections on a planar base and pre-associating a multiple color reference scheme with a property test substance of a respective one of the test sections. The method further includes the procedures of visual color comparison in order to match a reaction color of the property test substance, with a selected one of different colors of the multiple color reference scheme and determining a respective one of the values according to the outcome of the procedure of matching.

In accordance with a further aspect of the disclosed technique, there is thus provided a method for determining the value of a plurality of properties of a liquid. The method includes the procedures of providing a plurality of test sections, each located on the inner wall of a respective one of a plurality of containers and pre-associating a multiple color reference scheme with a property test substance of a respective one of the test sections. The method further includes the procedures of matching a reaction color of the property test substance, with a selected one of different colors of the multiple color reference scheme and determining a respective one of the values according to the outcome of the procedure of matching.

In yet another aspect of the present invention, a liquid testing device for comparing the value of each of a plurality of properties of a liquid with a reference value is disclosed, the device comprising a planar base, a plurality of test sections, located on the planar base, the test sections including, a test sub-section which exhibits a color according to the value, as a result of reaction of a reagent with the liquid, a reference color section located adjacent to the test sub-section, the reference color section including at least one reference color corresponding the reference value. The reference value may be a maximum acceptable value or a minimum acceptable value. The reference value may be printed adjacent to the reference color. The test section may further comprise a label respective of a property of the liquid. The test sub-section may be impregnated with the reagent. The reference section may include at least two reference-colored sub sections. The reference section may include a limit line.

In another aspect of the invention, a method for comparing values of a plurality of properties of a liquid to a plurality of reference values is presented, the method comprising the procedures of providing a plurality of test sections on a planar base, pre-associating a color from a reference color scheme including at least one reference color with a property test substance of a respective one of the test sections, immersing the planar base in the fluid to obtain a reaction color of the property test substance, and comparing the reaction color of the property test substance, with the at least one reference color. The method further comprises the reference color scheme including a maximum acceptable value or a minimum acceptable value.

According to another aspect of the present invention, a liquid testing device for determining the value of at least one property of a liquid is disclosed, the device comprising a planar base, and at least one test section, located on the planar base, with the test section including a test sub-section which exhibits a color according to the value, as a result of reaction of a reagent with the liquid, and a reference color section located adjacent to the test sub-section, with the reference color section including at least one reference color. The value may be determined by matching one of the at least one reference color with the reaction color. The test section may further comprise a label respective of a property of the liquid. The test sub-section may be impregnated with the reagent. The at least one property may be a concentration of a substance in the liquid. The test section further comprises a value indicating section, and the value indicating section may include at least one number, with the one number being located adjacent to the at least one reference color, wherein the at least one number may represent a selected value of a property of the liquid.

The important features of the invention are summarized as follows:

1. A multiple of tests can be performed simultaneously.
2. The testing device is integrated and self-contained.
3. The visual matching is a quicker procedure, during which the reaction color remains stable.
4. The test sub-section is arranged to encompass the entire reference section having the plurality of different reference colors, and there is contact between them.
5. The test is performed by a single, one-step procedure of immersion, reaction and color reading.
6. The reaction color becomes substantially visually merged with one of the different reference colors due to self-alignment therebetween, making for greater accuracy and less error in reading the test results.
7. There is no need for physical alignment of the test sub-section reaction color and the reference colors, and there is no dripping or mess during the color reading.

In the test strips field, the inventive testing device overcomes the existing obstacles, by enabling a quicker test procedure of several parameters simultaneously. The one-step procedure overcomes the problem of stability of the color reaction during the visual reading of the test results, by placement of the reference color scale adjacent to and in contact with the test sub-section.

The inventive testing device and the one-step test procedure transform the procedure of liquid testing to a simpler, more efficient, quicker and more accurate procedure, for the unskilled user, and for the skilled user as well.

For the products available in the liquid testing market by the major manufacturers and distributors, there is no product in which the test sub-section is adjacent to and in contact with the reference color scale, in a way which enables the visual reading of the test results to be more accurate, and simpler for several parameters simultaneously.

The quick, routine testing of liquid properties, such as water parameters, is a widely used technique. The fact is that the many large manufacturers of test devices, including test strips, did not produce and develop the inventive testing device. If the inventive testing device would have been apparent as a natural development based on prior art, these companies would have already developed it, but this is not the case.

In fact, the simplicity of combining several tests on one strip with adjacent color scales constitutes a complicated testing device due to the manufacturing process, requiring costly, high quality, and stable color scale printing for achieving test accuracy.

An integrated, multi-test device for simultaneous immediate and accurate determination of a plurality of liquid properties should quickly become a great success, and the absence of such a simple and useful device on the market today clearly demonstrates the creativity and advancement of the inventive testing device.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS OF THE INVENTION

The disclosed technique overcomes the disadvantages of the prior art by providing a test medium in which the color of the liquid changes as a result of reaction with a plurality of test substances, and the user determines a respective property of the liquid, by matching a respective resultant color with a respective color index. A battery of associated pairs of test sections and reference color schemes can be placed side by side, such as on a card, whereby the user determines the concentration of different substances in the liquid, by immersing the card in the liquid and matching the color of the test section with the reference color scheme. Each test section is impregnated with a selected substance, whereby the reaction of the selected substance with the liquid enables the user to determine the concentration of another selected substance in the liquid.

Figure 1A:
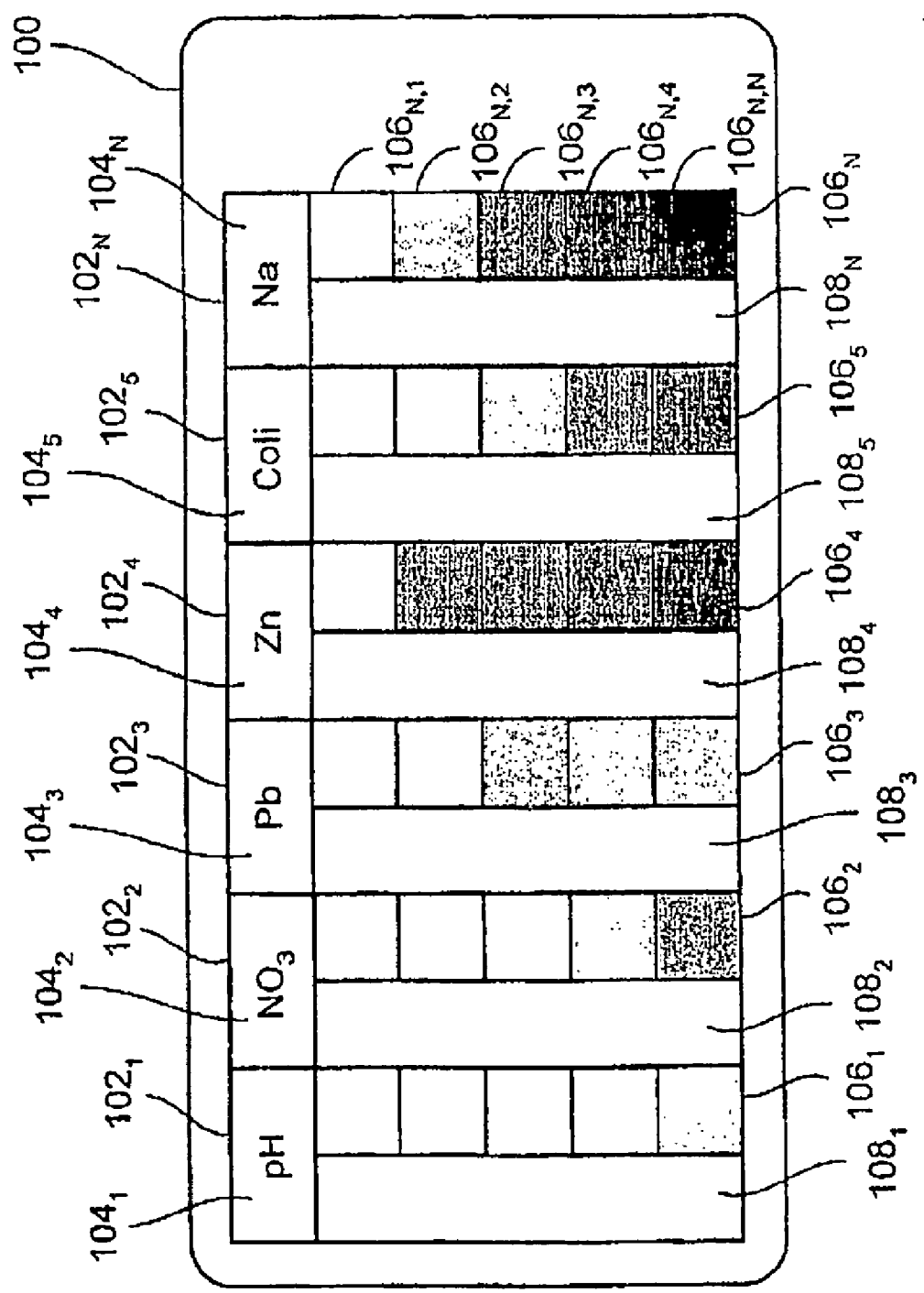
FIG. 1A is a schematic illustration of a liquid testing device, constructed and operative in accordance with an embodiment of the disclosed technique.
Figure 1B:
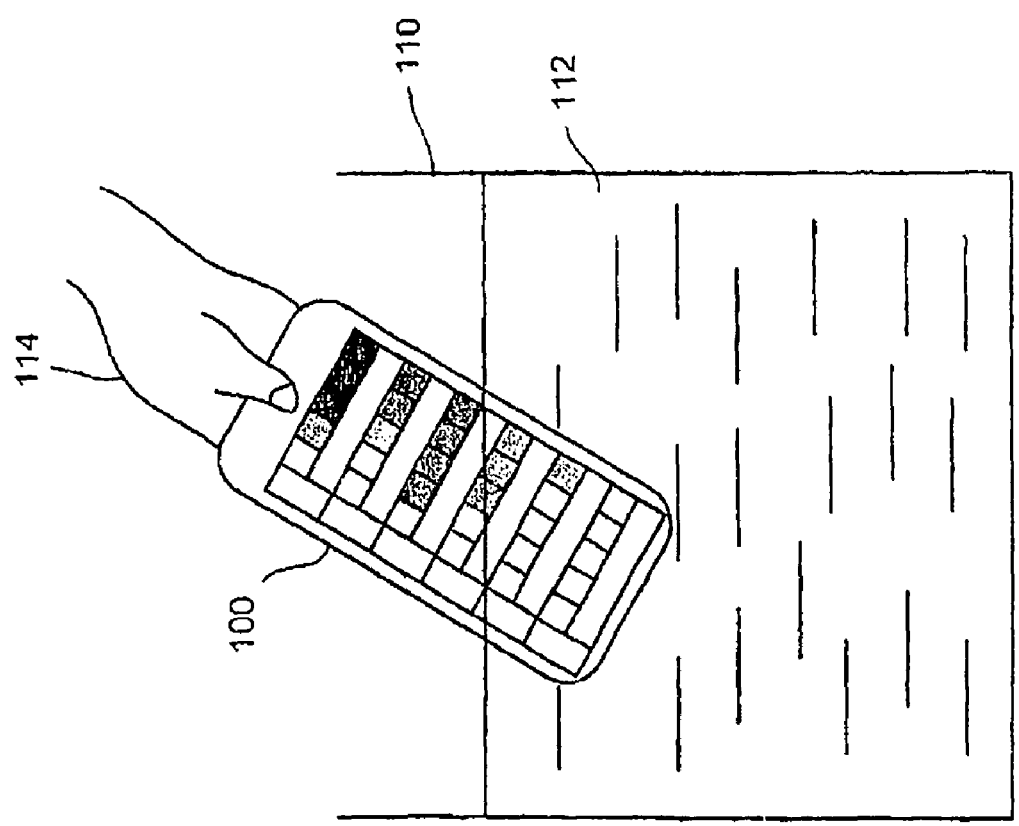
FIG. 1B is a schematic illustration of the liquid testing device of FIG. 1A being immersed in a liquid.
Figure 1C:
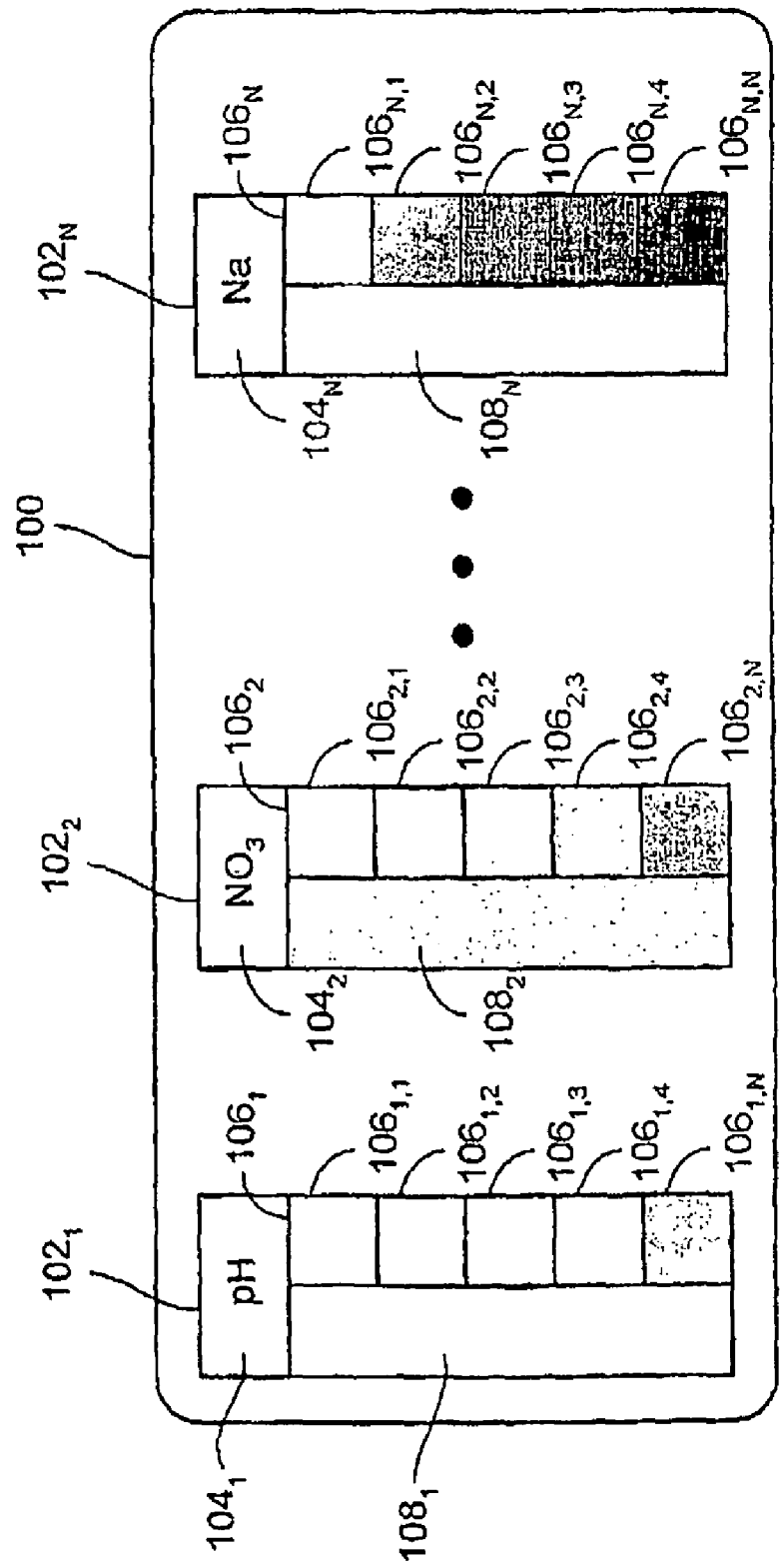
FIG. 1C is a schematic illustration of the liquid testing device of FIG. 1A, wherein the colors of the test sections have changed, after immersion of the liquid testing device in the liquid.

Reference is now made to FIGS. 1A, 1B and 1C. FIG. 1A is a schematic illustration of a liquid testing device, generally referenced 100, constructed and operative in accordance with an embodiment of the disclosed technique. FIG. 1B is a schematic illustration of the liquid testing device of FIG. 1A being immersed in a liquid. FIG. 1C is a schematic illustration of the liquid testing device of FIG. 1A, wherein the colors of the test sections have changed, after immersion of the liquid testing device in the liquid.

With reference to FIG. 1A, liquid testing device 100 includes a plurality of test sections $102_1$, $102_2$, $102_3$, $102_4$, $102_5$ and $102_N$. Test sections $102_1$, $102_2$, $102_3$, $102_4$, $102_5$ and $102_N$ include label sections $104_1$, $104_2$, $104_3$, $104_4$, $104_5$ and $104_N$, reference schemes $106_1$, $106_2$, $106_3$, $106_4$, $106_5$ and $106_N$, and test sub-sections $108_1$, $108_2$, $108_3$, $108_4$, $108_5$ and $108_N$, respectively. Each reference color scheme further includes a plurality of reference colored sub-sections, each of which is in a different color. For example, reference color scheme $106_N$ includes reference colored sub-sections $106_{N,1}$, $106_{N,2}$, $106_{N,3}$, $106_{N,4}$ and $106_{N,N}$, which are in different shades of blue. According to the example set forth in FIG. 1A, reference color schemes $106_1$, $106_2$, $106_3$, $106_4$ and $106_5$ include reference colored sub-sections in different shades of brown, yellow, green, turquoise and purple, respectively.

Generally, a color can be defined according to a hue (e.g., blue, green, red, yellow, and the like), a saturation level and a brightness level. The saturation level defines the concentration of a specific hue. The brightness level defines the level of brightness or darkness of the hue. For example, a yellow oil paint consists of a mixture of linseed oil and lead chromate. The linseed oil allows the paint to flow and the lead chromate renders a yellow color to the oil paint. The saturation level of the yellow oil paint is defined by the amount of lead chromate in a given volume of linseed oil. The brightness level of the yellow oil paint is defined by the amount of white lead (for whiteness) or charcoal (for darkness) in the given volume of linseed oil.

It is noted that some or all of the reference colored sub-sections in a given test section can be in different hues (e.g., blue, green, red, yellow, and the like). Alternatively, all the reference colored sub-sections in a given test section can be in the same hue, but each having a different saturation level, brightness level, or both (e.g., each of the reference colored sub-sections of a given test section being a different shade of red).

Each of the label sections $104_1$, $104_2$, $104_3$, $104_4$, $104_5$ and $104_N$ indicates a property of the liquid or a substance in the liquid, whose concentration can be determined by matching the color of the respective test sub-section with the color of one of the reference colored sub-sections of the respective reference color scheme. In the example set forth in FIG. 1A, test section $102_1$ is constructed to test the pH of water and test sections $102_2$, $102_3$, $102_4$, $102_5$ and $102_N$ are constructed to test the concentration of nitrate ($NO_3$), lead (Pb), zinc (Zn), Escherichia Coli (E. Coli) and sodium (Na), respectively, in water as well as in other liquids such as liquid fuel, crude oil, urine, body liquids and blood components, food and beverages, water solutions of any kind, and the like.

It is noted that sedimentation, the presence of general or specific bacteria, and concentration of hydrogen sulfide and nitrite ($NO_2$) can also be determined.

It is further noted that other substances which can be tested by the test strip method include: aluminum, ammonia, arsenic, ascorbic acid, bromine, calcium, carbonate, chloride, cobalt, cyanide, fluoride, formaldehyde, glycol, iodine, manganese, molybdenum, nickel, mercury, peraceric acid, peroxide, phosphate, potassium, sulfate, sulfite, tin, permanganate, pesticide, cyanuric acid, protein, glucose, ketones, urobilinogen, bilirubin, leucocytes, chlorochromate, specific gravity, oxidants, pyridinium, creatinine, glutaraldehyde, ammonium, chromate, metals, chromium, alkalinity, hardness, silver, salt, pH, acidity and the like. These tests can be conducted in water as well as in liquids other than water (as mentioned above) by reagents imprinted on a card according to the disclosed technique.

Liquid testing device 100 is made of a material, which substantially remains stable after being immersed in the liquid. For this purpose, liquid testing device 100 can be made of a flexible polymer, rigid polymer, glass, paper, plastic coated paper, cardboard, timber, dry clay, ceramic, masonry, leather, textile, metal, fabricated materials, and the like. Liquid testing device 100 is a substantially thin sheet in the form of rectangle, square, triangle, rhombus, parallelogram, trapezoid, quadrilateral, circle, annulus, ellipse, sector of a circle, freeform closed curve, and the like. Geometrically, the thin sheet is a plane which can either be flat or warped (i.e., rolled, folded, twisted, convex, concave, and the like).

Each test sub-section is impregnated with a test substance whose reaction with the liquid causes the color of the test sub-section to change, whereby the new color of the test sub-section indicates the concentration of a selected substance in the liquid or the concentration of a selected property of the liquid under test.

With reference to FIG. 1B, a container 110 contains a liquid 112 which is to be tested. User 114 immerses liquid testing device 100 in the liquid 112 and waits for the test substances in each of the test sub-sections $108_1$, $108_2$, $108_3$, $108_4$, $108_5$ and $108_N$ to react with the liquid.

With reference to FIG. 1C, reference colored sub-sections $106_{1,1}$, $106_{1,2}$, $106_{1,3}$, $106_{1,4}$ and $106_{1,N}$ designate pH levels of 9, 8, 7, 6 and 5, respectively. Reference colored sub-sections $106_{2,1}$, $106_{2,2}$, $106_{2,3}$, $106_{2,4}$ and $106_{2,N}$ designate nitrate concentrations of 14, 12, 10, 8 and 6 milligram per liter (mg/l), respectively. Reference colored sub-sections $106_{N,1}$, $106_{N,2}$, $106_{N,3}$, $106_{N,4}$ and $106_{N,N}$ designate sodium concentrations of 16, 15, 14, 13 and 12 mg/l, respectively.

In the following description, liquid 112 is water. When liquid 112 reacts with the test substance which is impregnated in test sub-section $108_1$, the color of test sub-section $108_1$ changes to a hue which corresponds to the pH level of liquid 112. When liquid 112 reacts with the test substance which is impregnated in test subsection $108_2$, the color of test sub-section $108_2$ changes to a hue which corresponds to the nitrate level of liquid 112. When liquid 112 reacts with the test substance which is impregnated in test sub-section $108_N$, the color of test sub-section $108_N$ changes to a hue which corresponds to the sodium level of liquid 112. User 114 reads the concentration of a selected substance in water, by matching the color of the test sub-section, with the color of one of the reference colored sub-sections of the respective reference color scheme, It is noted that since the test sub-section color becomes substantially visually merged with the matching reference color, the matching process is a straight forward operation and that the user does not have to align the test sub-sections with the reference colored sub-sections.

For example, user 114 compares the color of test sub-section $108_1$ with reference colored sub-sections $106_{1,1}$, $106_{1,2}$, $106_{1,3}$, $106_{1,4}$ and $106_{1,N}$ and determines that the color of test sub-section $108_1$ is substantially similar to the color of reference colored sub-section $106_{1,3}$. Thus, user 114 determines that the pH of liquid 112 is 7. User 114 compares the color of test sub-section $108_2$ with reference colored sub-sections $106_{2,1}$, $106_{2,2}$, $106_{2,3}$, $106_{2,4}$ and $106_{2,N}$ and determines that the color of test sub-section $108_2$ is substantially similar to the color of reference colored sub-section $106_{2,4}$. Thus, user 114 determines that the concentration of nitrate in liquid 112 is 8 mg/l. User 114 compares the color of test sub-section $108_N$ with reference colored sub-sections $106_{N,1}$, $106_{N,2}$, $106_{N,3}$, $106_{N,4}$ and $106_{N,N}$ and determines that the color of test sub-section $108_N$ is substantially similar to the color of reference colored sub-section $106_{N,1}$. Thus, user 114 determines that the concentration of sodium in liquid 112 is 16 mg/l. It is noted that a substantially large number of test sections $102_1$, $102_2$ and $102_N$ can be constructed on liquid testing device 100, thus enabling the testing of a substantially large number of properties and substance concentrations in the liquid, simultaneously.

Figure 7:
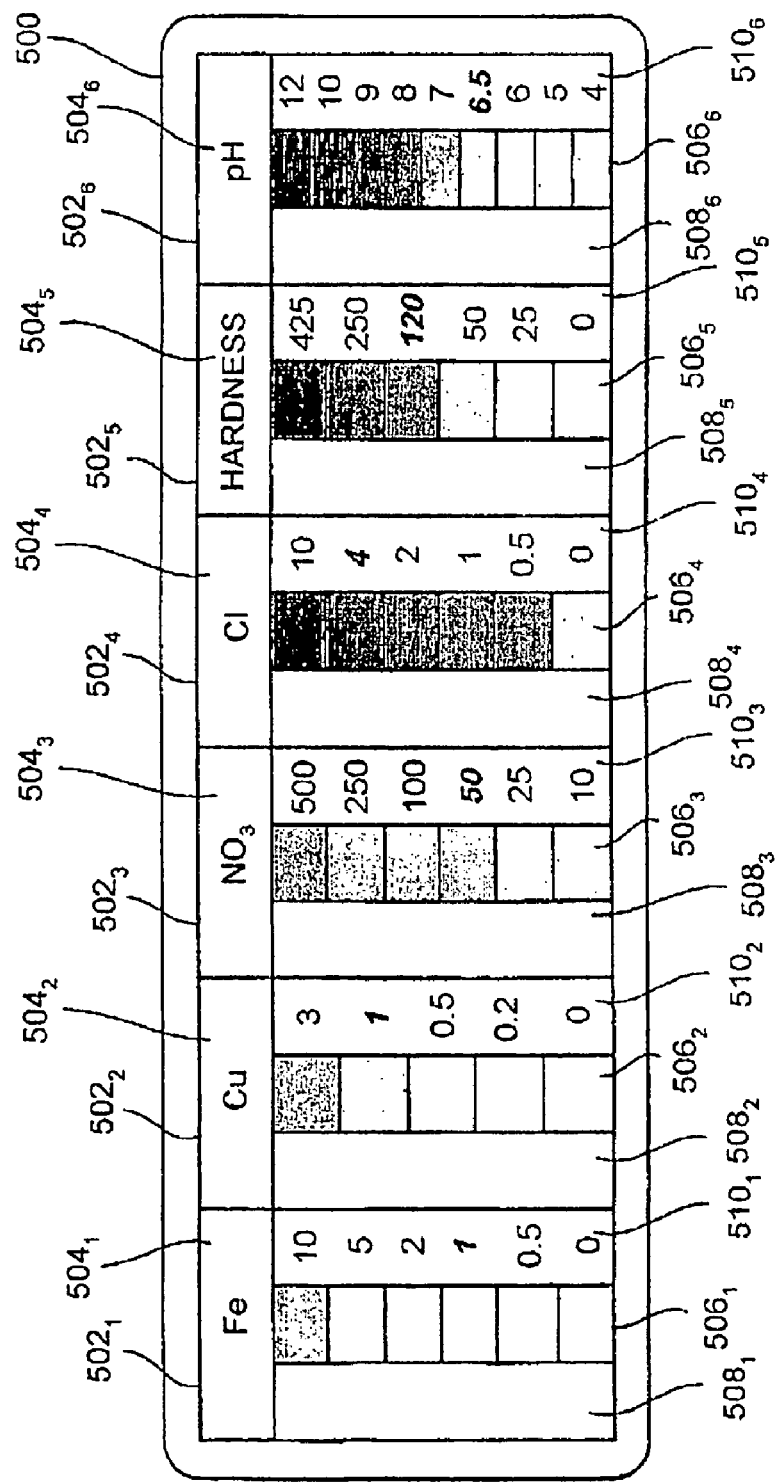
FIG. 7 is a schematic illustration of a liquid testing device, constructed and operative in accordance with a further embodiment of the disclosed technique.

The invention is not limited to determining a plurality of properties of a liquid. Accordingly, it is within the scope of the invention to also provide a liquid testing device including only one test section that includes a test sub-section exhibiting a color according to a value of a property tested as a result of the reaction of a reagent with liquid, and adjacent to the test sub-section there is located a reference color scheme section that can include one or more colors. The liquid testing device may further include a value indicating section, as shown in the view of FIG. 7 described below, including one or more values of properties, with the value indicating section being adjacent to a reference color section including one or more reference colors. Such an arrangement can be used when one more values of properties are determined with a liquid testing device.

Figure 2A:
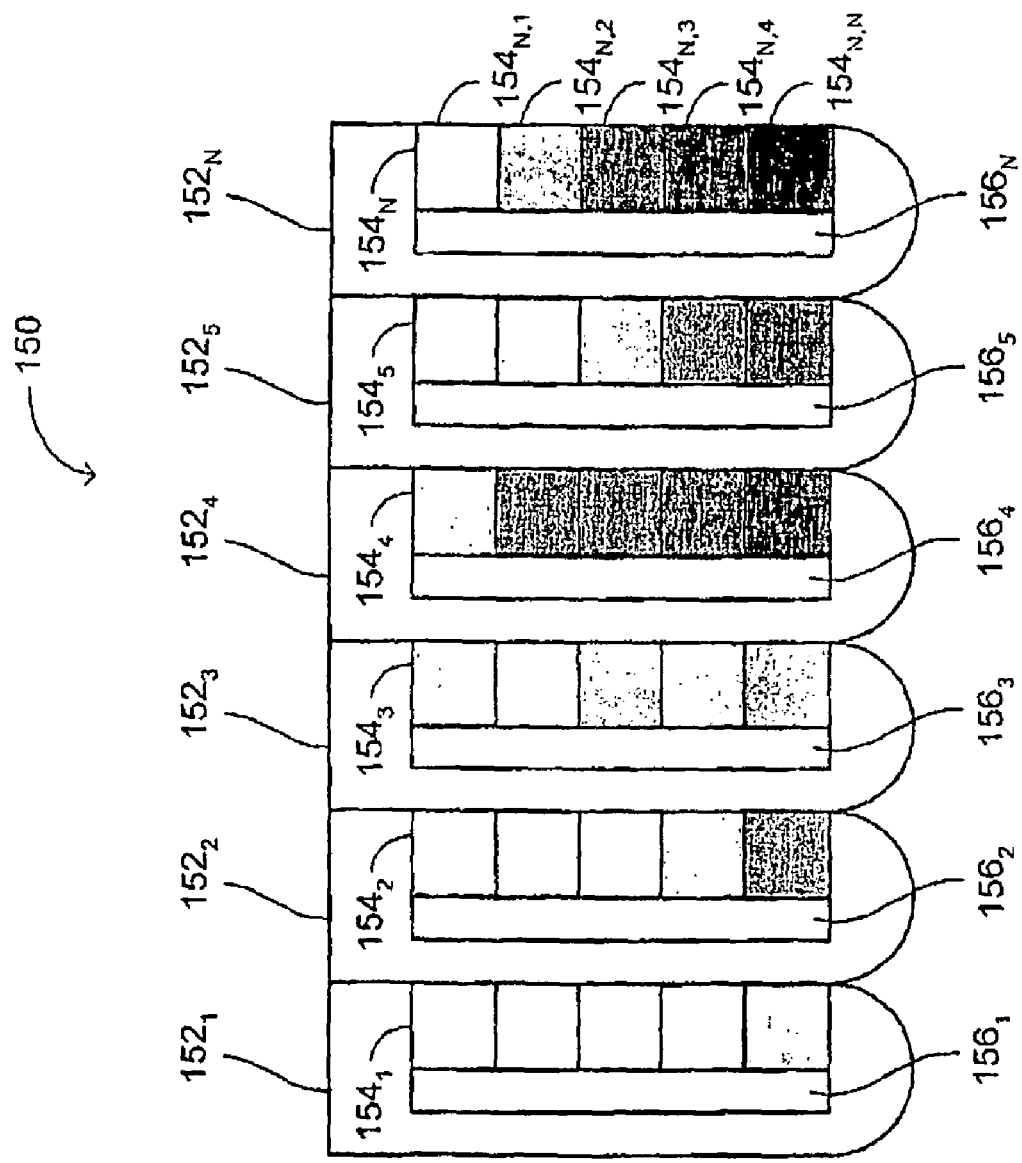
FIG. 2A is a schematic illustration of a battery of containers, constructed and operative in accordance with another embodiment of the disclosed technique.
Figure 2B:
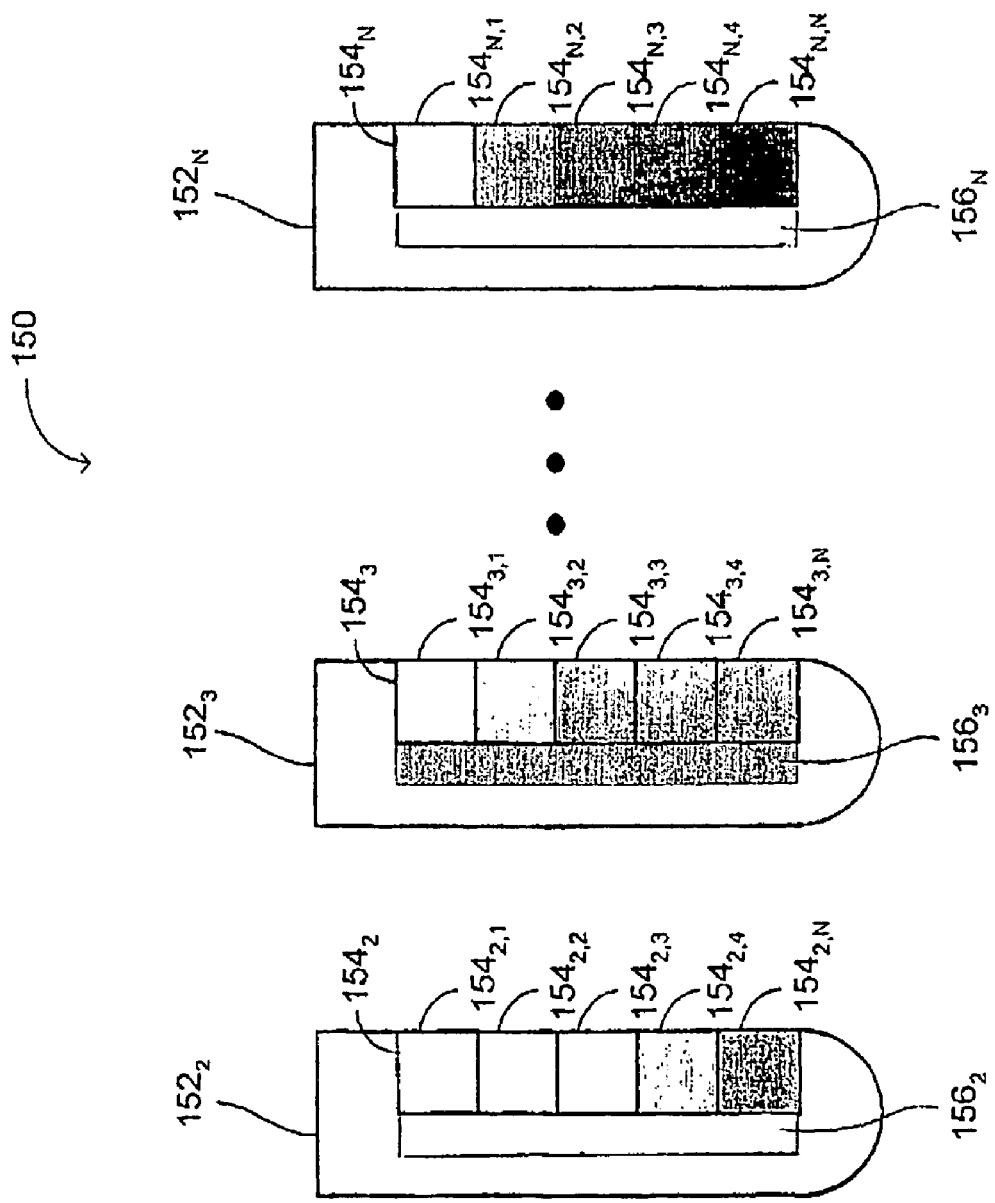
FIG. 2B is a schematic illustration of the containers of FIG. 2A, after reaction of a liquid with the test substance of the test sub-section of each container.

Reference is now made to FIGS. 2A and 2B. FIG. 2A is a schematic illustration of a battery of containers, generally referenced 150, constructed and operative in accordance with another embodiment of the disclosed technique. FIG. 2B is a schematic illustration of the containers of FIG. 2A, after reaction of a liquid with the test substance of the test sub-section of each container.

The battery of containers 150, includes a plurality of containers $152_1$, $152_2$, $152_3$, $152_4$, $152_5$ and $152_N$. Each of containers $152_1$, $152_2$, $152_3$, $152_4$, $152_5$ and $152_N$ is constructed separately and are fastened together, by an adhesive, at least one fastener, welding, and the like. Alternatively, containers $152_1$, $152_2$, $152_3$, $152_4$, $152_5$ and $152_N$ are constructed as separate cavities within a single body.

Containers $152_1$, $152_2$, $152_3$, $152_4$, $152_5$ and $152_N$ include reference schemes $154_1$, $154_2$, $154_3$, $154_4$, $154_5$ and $154_N$ and test sub-sections $156_1$, $156_2$, $156_3$, $156_4$, $156_5$ and $156_N$, respectively. Each reference color scheme further includes a plurality of reference colored sub-sections, each of which is in a different color. For example, reference scheme $154_N$ includes reference colored sub-sections $154_{N,1}$, $154_{N,2}$, $154_{N,3}$, $154_{N,4}$ and $154_{N,N}$, which are in different shades of blue. According to the example set forth in FIG. 2A, reference color schemes $154_1$, $154_2$, $154_3$, $154_4$ and $154_5$ include reference colored sub-sections in different shades of brown, yellow, green, turquoise, purple and blue, respectively. Each of the test sub-sections $156_1$, $156_2$, $156_3$, $156_4$, $156_5$ and $156_N$ is impregnated with a test substance, selected to determine the concentration of a selected substance in the liquid or the value of a selected property of the liquid.

One end of each of containers $152_1$, $152_2$, $152_3$, $152_4$, $152_5$ and $152_N$ is entirely or partially open, in order to allow the user to let the liquid into the container. Each of containers $152_1$, $152_2$, $152_3$, $152_4$, $152_5$ and $152_N$ can be closed by a matching stopper (not shown), in order to allow the user to shake the container and for the reaction between the test substance and the liquid to take place. Alternatively, the stoppers of containers $152_1$, $152_2$, $152_3$, $152_4$, $152_5$ and $152_N$ are part of a single body.

Test sub-sections $156_1$, $156_2$, $156_3$, $156_4$, $156_5$ and $156_N$ are transparent strips which are fastened to the inner wall of containers $152_1$, $152_2$, $152_3$, $152_4$, $152_5$ and $152_N$, respectively. Test sub-sections $156_1$, $156_2$, $156_3$, $156_4$, $156_5$ and $156_N$ are located adjacent to reference schemes $154_1$, $154_2$, $154_3$, $154_4$, $154_5$ and $154_N$, respectively.

The cross section of each of containers $152_1$, $152_2$, $152_3$, $152_4$, $152_5$ and $152_N$, along either the longitudinal axis or the transverse axis thereof, can be either variable or constant. This cross section can be in the form of rectangle, square, triangle, rhombus, parallelogram, trapezoid, quadrilateral, circle, annulus, ellipse, sector of a circle, freeform closed curve, and the like.

Each of containers $152_1$, $152_2$, $152_3$, $152_4$, $152_5$ and $152_N$ is made of a polymer, glass, timber, dry clay, ceramic, masonry, metal, and the like, having at least one transparent portion. If the container is opaque, then that portion of the container which covers a test sub-section, is enhanced by a transparent property or is made of a transparent material, Hence, the user can compare the color of a test sub-section with the colors of the respective reference colored sub-sections.

When the test substance of a test sub-section reacts with the liquid, the color of the test sub-section changes to a color substantially similar to the color of one of the reference colored sub-sections in the respective reference color scheme. The user then determines the value of the selected property of the liquid or the concentration of the selected substance in the liquid, by matching the new color of the test sub-section, with the color of one of the reference colored sub-sections.

With reference to FIG. 2B, containers $152_2$, $152_3$ and $152_N$ include reference color schemes $154_2$, $154_3$ and $154_N$, respectively. Reference color scheme $154_2$ includes reference colored sub-sections $154_{2,1}$, $154_{2,2}$, $154_{2,3}$, $154_{2,4}$ and $154_{2,N}$. Reference color scheme $154_3$ includes reference colored sub-sections $154_{3,1}$, $154_{3,2}$, $154_{3,3}$, $154_{3,4}$ and $154_{3,N}$. Reference color scheme $154_N$ includes reference colored sub-sections $154_{N,1}$, $154_{N,2}$, $154_{N,3}$, $154_{N,4}$ and $154_{N,N}$.

The liquid which is to be tested, is poured in containers $152_2$, $152_3$ and $152_N$. The test substances in test sub-sections $156_2$, $156_3$ and $156_N$ react with the liquid and the color of each of test sub-sections $156_2$, $156_3$ and $156_N$ in each container changes to the color of one of the reference colored sub-sections in the respective reference color scheme. In the example set forth in FIG. 2B, container $152_2$ is designated to test the concentration of nitrate in the liquid (see FIG. 1C). The user matches the color of test sub-section $156_2$ with reference colored sub-section $154_{2,2}$ and determines that the concentration of nitrate in the liquid is 12 mg/l.

Container $152_3$ is designated to test for example, the concentration of lead in the liquid. Reference colored sub-sections $154_{3,1}$, $154_{3,2}$, $154_{3,3}$, $154_{3,4}$ and $154_{3,N}$ designate lead concentrations of 0.0122, 0.0124, 0.0126, 0.0128 and 0.0130 mg/l, respectively, in the liquid. The user matches the color of test sub-section $156_3$ with reference colored sub-section $154_{3,4}$ and thus, determines that the concentration of lead in the liquid is 0.0128 mg/l.

Container $152_N$ is designated to test the concentration of sodium in the liquid (see FIG. 1C). The user matches the color of test sub-section $156_N$ with reference colored sub-section $154_{N,1}$ and thus, determines that the concentration of sodium in the liquid is 16 mg/l.

Figure 3:
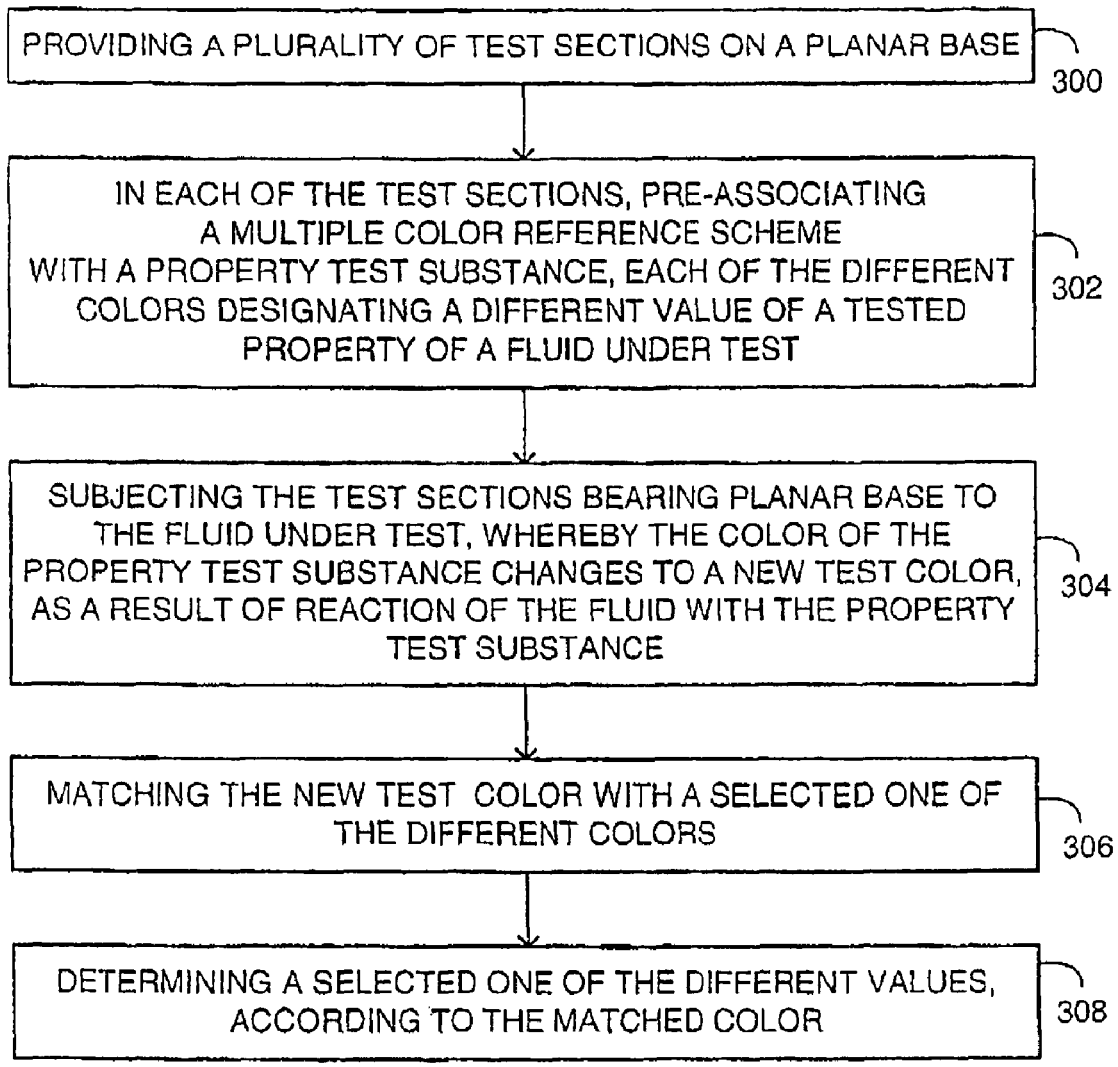
FIG. 3 is a schematic illustration of a method for determining a quantitative property of a liquid, operative in accordance with a further embodiment of the disclosed technique.

Reference is now made to FIG. 3, which is a schematic illustration of a method for determining a quantitative property of a liquid, operative in accordance with a further embodiment of the disclosed technique. In procedure 300, a plurality of test sections are provided on a planar base. With reference to FIG. 1A, test sections $102_1$, $102_2$, $102_3$, $102_4$, $102_5$ and $102_N$ are provided to test card 100.

In procedure 302, a multiple color reference scheme is pre-associated with a property test substance in each of the test sections, wherein each of the different colors designates a different value of a tested property of a liquid under test. With reference to FIG. 1A, reference schemes $106_1$, $106_2$, $106_3$, $106_4$, $106_5$ and $106_N$ of liquid testing device 100, are placed adjacent to test sub-sections $108_1$, $108_2$, $108_3$, $108_4$, $108_5$ and $108_N$, respectively. Each of test sub-sections $108_1$, $108_2$, $108_3$, $108_4$, $108_5$ and $108_N$ includes a selected test substance, to test the level of another substance in a liquid. For example, reference scheme $106_N$ is placed adjacent to test sub-section $108_N$. Reference scheme $106_N$ is colored in different shades of blue, as illustrated by reference colored sub-sections $106_{N,1}$, $106_{N,2}$, $106_{N,3}$, $106_{N,4}$ and $106_{N,N}$. Reference scheme $106_N$ is employed to determine the concentration of sodium and each of the reference colored sub-sections $106_{N,1}$, $106_{N,2}$, $106_{N,3}$, $106_{N,4}$ and $106_{N,N}$ designates a different sodium concentration in the liquid.

In procedure 304, the test sections bearing planar base is subjected to the liquid under test, whereby the color of the property test substance changes to a new test color, as a result of reaction of the liquid with the property test substance. With reference to FIGS. 1A and 1B, liquid testing device 100 is immersed in liquid 112, whereby liquid 112 reacts with the test substance included in test sub-section $108_N$ and the color of test sub-section $108_N$ (and the liquid which was absorbed by test sub-section $108_N$), changes to a new color.

In procedure 306, the new test color is matched with a selected one of the different colors. With reference to FIG. 1C, the user matches the color of test sub-section $108_N$ with reference colored sub-section $106_{N,1}$.

In procedure 308, a selected one of the different values is determined, according to the matched color. With reference to FIG. 1C, the user determines that the concentration of sodium (i.e., the property under test) in the liquid, is 16 mg/l.

Figure 4:
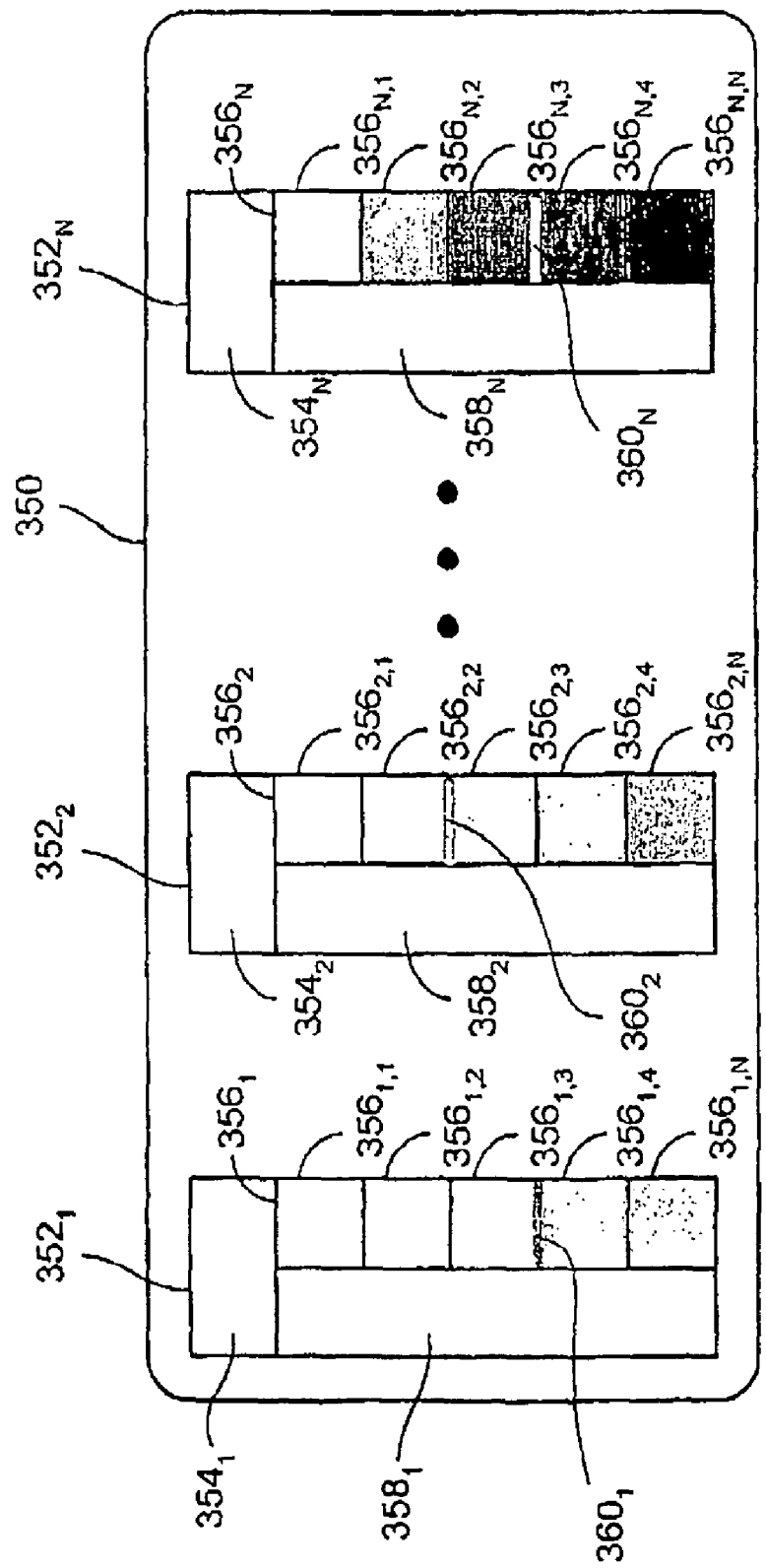
FIG. 4 is a schematic illustration of a liquid testing device, constructed and operative in accordance with another embodiment of the disclosed technique.

Reference is now made to FIG. 4, which is a schematic illustration of a liquid testing device, generally referenced 350, constructed and operative in accordance with another embodiment of the disclosed technique. Liquid testing device 350 includes a plurality of test sections $352_1$, $352_2$ and $352_N$. Test section $352_1$ includes a label section $354_1$, a reference scheme $356_1$ and a test sub-section $358_1$. Reference scheme $356_1$ includes a plurality of reference colored sub-sections $356_{1,1}$, $356_{1,2}$, $356_{1,3}$, $356_{1,4}$ and $356_{1,N}$ and a limit line $360_1$.

Test section $352_2$ includes a label section $354_2$, a reference color scheme $356_2$ and a test sub-section $358_2$. Reference color scheme $356_2$ includes a plurality of reference colored sub-sections $356_{2,1}$, $356_{2,2}$, $356_{2,3}$, $356_{2,4}$ and $356_{2,N}$ and a limit line $360_2$. Test section $352_N$ includes a label section $354_N$, a reference color scheme $356_N$ and a test subsection $358_N$. Reference color scheme $356_N$ includes a plurality of reference colored sub-sections $356_{N,1}$, $356_{N,2}$, $356_{N,3}$, $356_{N,4}$ and $356_{N,N}$ and a limit line $360_N$.

Limit line $360_1$ is located between reference colored sub-sections $356_{1,3}$ and $356_{1,4}$. Limit line $360_2$ is located between reference colored sub-sections $356_{2,2}$ and $356_{2,3}$. Limit line $360_N$ is located between reference colored sub-sections $356_{N,3}$ and $356_{N,4}$.

Each limit line indicates to the user, that if the color of a test sub-section matches the color of one of the reference colored sub-sections which are located below the limit line, then the liquid under test, according to the tested property, is unacceptable for use. For example, if test section $352_1$ is employed to test the pH level of the liquid, and the color of test sub-section $358_1$ after immersion of liquid testing device 350 in the liquid, matches the color of reference colored sub-section $356_{1,4}$ or $356_{1,N}$, then the user determines that in both cases, the pH is below the allowable limit and thus the liquid is unacceptable for use.

Alternatively, the limit line indicates to the user, that if the color of a test sub-section matches the color of one of the reference colored sub-sections which are located above the limit line, then the liquid under test, according to the tested property, is unacceptable for use. For example, if test section $352_2$ is employed to test the concentration of nitrate in the liquid, and the color of test sub-section $358_2$ after immersion of liquid testing device 350 in the liquid, matches the color of reference colored sub-section $356_{2,1}$ or $356_{2,2}$, then the user determines that in both cases, the nitrate concentration is above the allowable limit and thus the liquid is unacceptable for use.

Figure 5A:
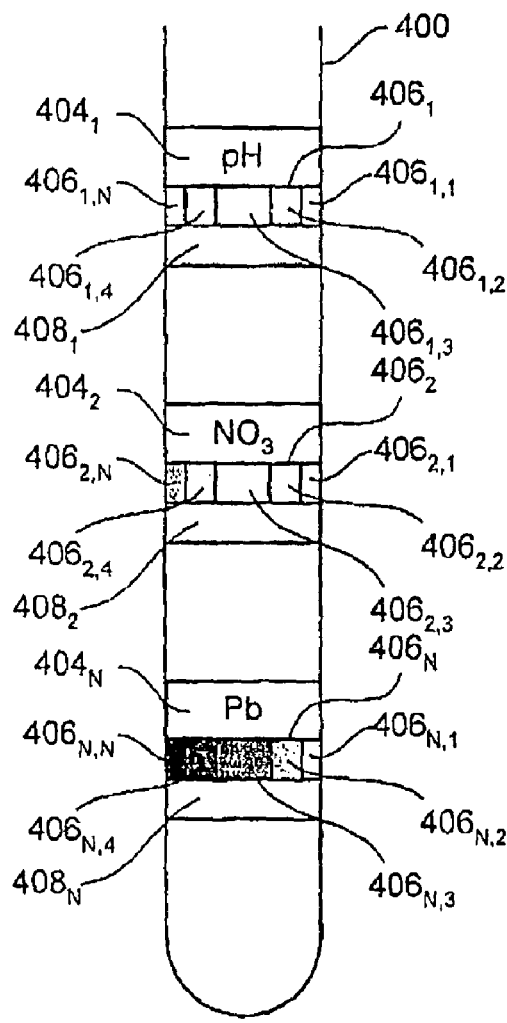
FIG. 5A is a schematic illustration of a container, constructed and operative in accordance with a further embodiment of the disclosed technique.
Figure 5B:
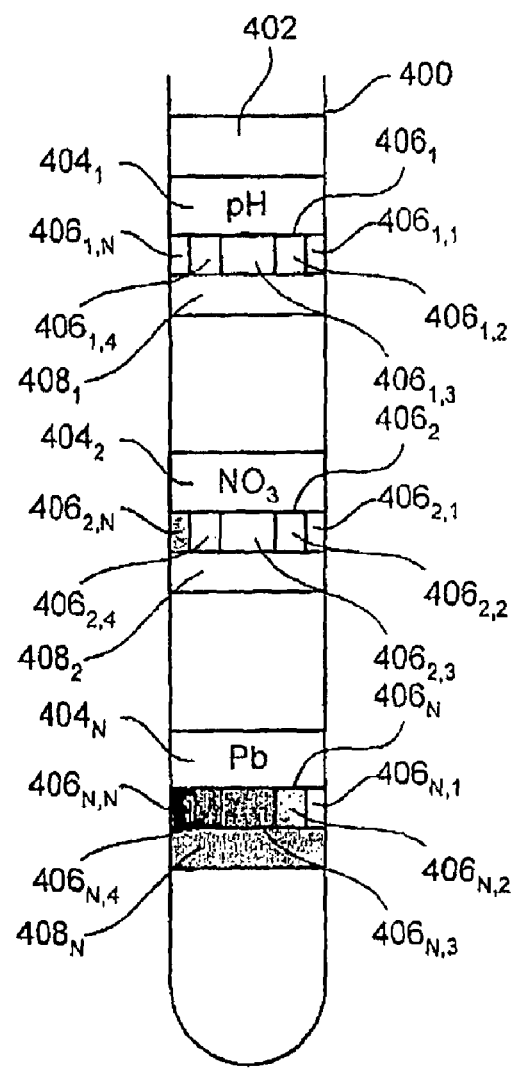
FIG. 5 is a schematic illustration of the container of FIG. 5A, after pouring a liquid in the container, wherein the liquid has reacted with different test substances.

Reference is now made to FIGS. 5A and 5B. FIG. 5A is a schematic illustration of a container, generally referenced 400, constructed and operative in accordance with a further embodiment of the disclosed technique. FIG. 5B is a schematic illustration of the container of FIG. 5A, after pouring a liquid in the container, wherein the liquid has reacted with different test substances. Container 400 includes a plurality of label sections $404_1$, $404_2$ and $404_N$, a plurality of reference color schemes $406_1$, $406_2$, $406_N$, and a plurality of test sub-sections $408_1$, $408_2$ and $408_N$.

Reference color scheme $406_1$ includes a plurality of reference colored sub-sections $406_{1,1}$, $406_{1,2}$, $406_{1,3}$, $406_{1,4}$ and $406_{1,N}$. Reference color scheme $406_2$ includes a plurality of reference colored sub-sections $406_{2,1}$, $406_{2,2}$, $406_{2,3}$, $406_{2,4}$ and $406_{2,N}$. Reference color scheme $406_N$ includes a plurality of reference colored sub-sections $406_{N,1}$, $406_{N,2}$, $406_{N,3}$, $406_{N,4}$ and $406_{N,N}$.

Each of the label sections $404_1$, $404_2$ and $404_N$ is printed on an inner wall of container 400, on an outer wall thereof or within the wall of container 400. Alternatively, each of the label sections $404_1$, $404_2$ and $404_N$ is in form of a transparent or an opaque pressure sensitive tape, which is adhered either to the inner wall of container 400, or to the outer wall thereof.

Reference color schemes $406_1$, $406_2$ and $406_N$ are located below label sections $404_1$, $404_2$ and $404_N$, respectively. Each of the reference color schemes $406_1$, $406_2$ and $406_N$ is printed on an inner wall of container 400, on an outer wall thereof or within the wall of container 400. Alternatively, each of the label sections $406_1$, $406_2$ and $406_N$ is in form of a transparent or an opaque pressure sensitive tape, which is adhered either to the inner wall of container 400, or to the outer wall thereof. Alternatively, reference color schemes $406_1$, $406_2$ and $406_N$ are located above label sections $404_1$, $404_2$ and $404_N$, respectively.

Each of test sub-sections $408_1$, $408_2$ and $408_N$ is a transparent strip which is impregnated with a test substance, wherein the transparent strip is fastened to the inner wall of container 400. Alternatively, each of test sub-sections $408_1$, $408_2$ and $408_N$ is a test substance in the form of a powder, which coats the inner wall of container 400. Test sub-sections $408_1$, $408_2$ and $408_N$ are located below reference color schemes $406_1$, $406_2$ and $406_N$, respectively. Test sub-sections $408_1$, $408_2$ and $408_N$ are located substantially adjacent to reference color schemes $406_1$, $406_2$ and $406_N$, respectively. Alternatively, test sub-sections $408_1$, $408_2$ and $408_N$ are located above reference color schemes $406_1$, $406_2$ and $406_N$, respectively.

With reference to FIG. 5B, when liquid 402 is poured in container 400, liquid 402 reacts with test sub-sections $408_1$, $408_2$ and $408_N$ and as a result of the reaction, the color of liquid 402 in the vicinity of each of the test sub-sections $408_1$, $408_2$ and $408_N$, changes. The user, then determines the value of each property of liquid 402, or the concentration of a substance in liquid 402, by matching the color of liquid 402 in the vicinity of test sub-sections $408_1$, $408_2$ and $408_N$, with the color of one of the reference colored sub-sections of reference schemes $406_1$, $406_2$ and $406_N$, respectively.

It is noted that after performing a liquid test, test sub-sections $408_1$, $408_2$ and $408_N$ can be removed from the inner wall of container 400 and a new set of test sections applied to the inner wall of container 400, thereby allowing the user to perform a new liquid test, by employing container 400 once again. Alternatively, the user can dispose of the container after performing a test and use another container for performing a new test. Each of the test sub-sections further includes a limit line, whereby the user can determine whether the liquid under test is acceptable for use according to a selected property, if the color of liquid after reaction, matches the color of one of the reference colored sub-sections, which is located either to the right or to the left of the limit line.

It is noted that different combinations of the relative locations of a label section, the respective reference scheme and the respective test sub-section, can be selected. Hence, the combinations described above are not exhaustive and other combinations are possible.

Figure 6A:
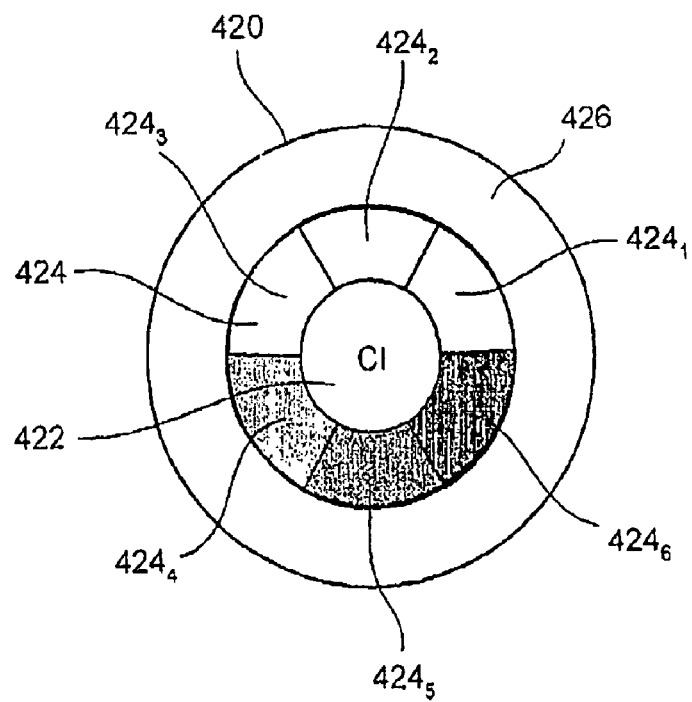
FIG. 6A is a schematic illustration of a test section, constructed and operative in accordance with another embodiment of the disclosed technique.
Figure 6B:
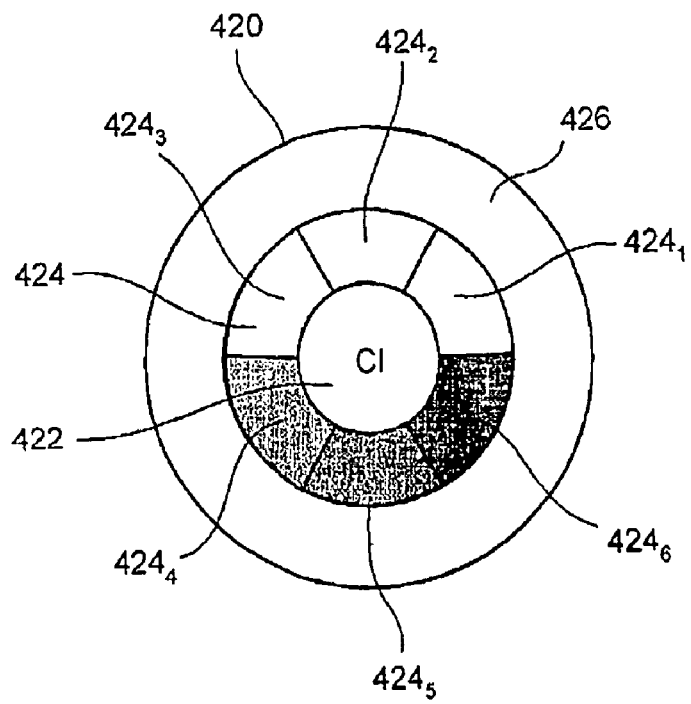
FIG. 6B is a schematic illustration of the test section of FIG. 6A, after a reaction of the test substance of the test sub-section with a liquid.

Reference is now made to FIGS. 6A and 6B. FIG. 6A is a schematic illustration of a test section, generally referenced 420, constructed and operative in accordance with another embodiment of the disclosed technique. FIG. 6B is a schematic illustration of the test section of FIG. 6A, after a reaction of the test substance of the test sub-section with a liquid.

With reference to FIG. 6A, test section 420 includes a label 422, a reference color scheme 424 and a test sub-section 426. Reference color scheme 424 includes a plurality of reference colored sub-sections $424_1$, $424_2$, $424_1$, $424_4$, $424_5$ and $424_6$. Test section 420 is in form of a circle. Label 422 is in form of a circle within test section 420. Reference color scheme 424 is in form of an annulus around label 422. Each of reference colored sub-sections $424_1$, $424_2$, $424_3$, $424_4$, $424_5$ and $424_6$ is a sector of the annulus of reference color scheme 424.

Test sub-section 426 is in form of an annulus surrounding reference scheme 424. Test sub-section 426 is impregnated with a selected test substance, in order to determine the concentration of a substance or the value of a property in the liquid.

According to the example set forth in FIG. 6A, test sub-section 426 is impregnated with a test substance to determine the concentration of chlorine. The centers of label 422, reference scheme 424 and test sub-section 426, lie at substantially the same point.

With reference to FIG. 6B, test sub-section 426 exhibits a color which matches the color of reference colored sub-section $424_2$. Thus, the user determines that the concentration of chlorine in the liquid is for example, 0.5 mg/l. It is noted that any geometric shape can be used for a test section, including a rectangle, an ellipse, abstract shapes, known trade marks, and the like.

Reference is now made to FIG. 7, which is a schematic illustration of a liquid testing device, generally referenced 500, constructed and operative in accordance with a further embodiment of the disclosed technique. Liquid testing device 500 includes a plurality of test sections $502_1$, $502_2$, $502_3$, $502_4$, $502_5$ and $502_6$. Test sections $502_1$, $502_2$, $502_3$, $502_4$, $502_5$ and $502_6$ include label sections $504_1$, $504_2$, $504_3$, $504_4$, $504_5$ and $504_6$, reference color schemes $506_1$, $506_2$, $506_3$, $506_4$, $506_5$ and $506_6$, test sub-sections $508_1$, $508_2$, $508_3$, $508_4$, $508_5$ and $508_6$, and value indicating sections $510_1$, $510_2$, $510_3$, $510_4$, $510_5$ and $510_6$, respectively.

Each reference color scheme further includes a plurality of reference colored sub-sections, each of which is in a different hue. A number is printed adjacent to each reference colored sub-section in each value indicating section. The material and geometry of liquid testing device 500 is similar to those of liquid testing device 100, as described herein above in connection with FIG. 1A. As an optional feature of the present invention, the number representing the value of the test can be marked (the value can be circled), for instance, with a pen for recording the tested value.

Test sections $502_1$, $502_2$, $502_3$, $502_4$, $502_5$ and $502_6$ are designated for testing the concentration of iron (Fe), copper (Cu), nitrate (NO$_3$), chlorine (Cl), and the hardness and pH of water, respectively. The numbers in each value indicating section represent different concentrations of the respective substance or different values of the respective parameter in the water under test.

Thus, the user reads the concentration of the substance or the value of the parameter, after comparing the color of a test sub-section with the respective reference color scheme and determining the reference colored sub-section which matches the color of the test sub-section. One of the numbers in each value indicating section is printed in a different style than the rest, thereby indicating the allowable concentration of a substance in water, or the allowable hardness or pH of water, according to a standard. For example, this number can be printed in bold, italics, be underlined, in a different color, in a different font, in a different size, and the like. It is noted that other properties of water can be determined, such as total alkalinity, and the like.

Figure 8A:
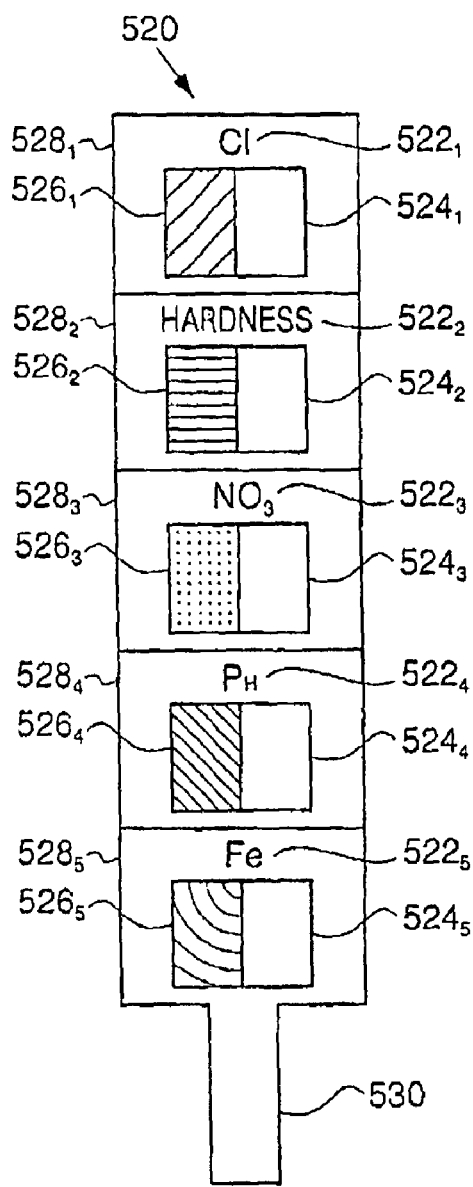
FIG. 8A is a schematic illustration of a liquid testing device, constructed and operative in accordance with another embodiment of the disclosed technique.

FIG. 8A presents a planar base liquid testing device 520. According to the embodiment shown in FIG. 8A, a liquid testing device 520 includes a plurality of test sections $528_1$, $528_2$, $528_3$, $528_4$, and $528_5$. Test sections $528_1$, $528_2$, $528_3$, $528_4$ and $528_5$ include label sections $522_1$, $522_2$, $522_3$, $522_4$, $522_5$, reference color schemes $526_1$, $526_2$, $526_3$, $526_4$, and $526_5$, and test sub-sections $524_1$, $524_2$, $524_3$, $524_4$, $524_5$. Liquid testing device 520 has a holding part 530 to be held by the user when immersing the device in tested liquid. Each of labels $522_1$, $522_2$, $522_3$, $522_4$, $522_5$ indicates a reagent or substance to be tested. Thus, the liquid testing device 520 presents the properties of a tested liquid.

According to the embodiment of FIG. 8A, liquid testing device 520 includes reference color schemes $526_1$, $526_2$, $526_3$, $526_4$, $526_5$ that have one color only for each of test sub-sections $528_1$, $528_2$, $528_3$, $528_4$, and $528_5$. This color may correspond, for example, to the maximum acceptable value of the tested substance. Accordingly, liquid testing device 520 is able to determine properties and substance concentrations within a liquid concurrently. A user (not shown) using liquid testing device 520 can compare the color of test sub-sections $524_1$, $524_2$, $524_3$, $524_4$, $524_5$ to reference color schemes $526_1$, $526_2$, $526_3$, $526_4$, $526_5$, respectively. One skilled in the art can appreciate that different reagents and materials can be tested for their concentration and presence by the liquid testing device 520. Furthermore, the number of test sections is not limited to the number shown in FIG. 8A and can be fewer or greater than the number shown.

According to one example of the present embodiment, a darker hue in test sub-section $524_5$ than reference color scheme $526_5$ will indicate a concentration of Iron (Fe) higher than allowed. Similarly, according to another example a lighter hue obtained in test-subsection $524_5$ than reference color scheme $526_5$ or alternatively an identical color as within reference color scheme $526_5$ will indicate an allowed concentration of Fe. The difference between test sub-sections $524_1$, $524_2$, $524_3$, $524_4$, $524_5$ and reference color schemes $526_1$, $526_2$, $526_3$, $526_4$, $526_5$ respectively, according to the embodiment is visible and can be indicated by a line drawn between test sub-sections and reference color schemes. One skilled in the art can appreciate that when other concentrations of other material are tested for their concentration within a liquid with a liquid testing device, a lighter hue can indicate an unacceptable concentration. Hence the hue of the reference color scheme according to the present embodiment corresponds to a crucial concentration, e.g. max. permitted value and a visual comparison shows whether the concentration in the tested liquid is above or below this value.

Figure 8B:
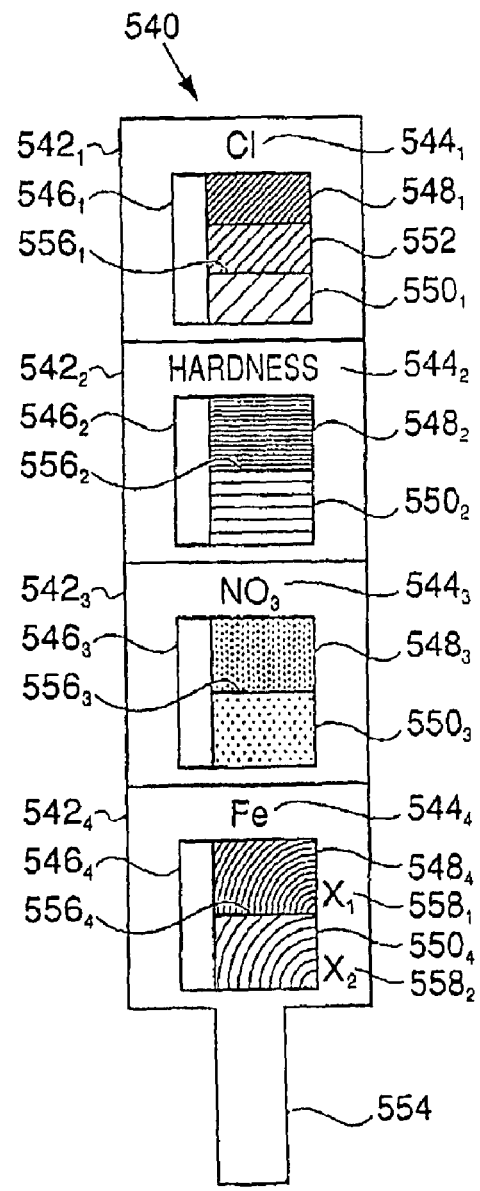
FIG. 8B is a schematic illustration of a liquid testing device, constructed and operative in accordance with another embodiment of the disclosed technique.

FIG. 8B is a schematic illustration of a liquid testing device 540 constructed and operative in accordance with yet another embodiment of the disclosed invention. Liquid testing device 540 has a holding part 554 that can be held by user when inserting said device in the tested liquid or removing it. Liquid testing device 540 includes a plurality of test sections $542_1$, $542_2$, $542_3$ and $542_4$. Test sections $542_1$, $542_2$, $542_3$, $542_4$ include label sections $544_1$, $544_2$, $544_3$, $544_4$ and test sub-sections $546_1$, $546_2$, $546_3$, $546_4$.

According to the present embodiment, the reference color scheme in each of the test sections $542_1$, $542_2$, $542_3$, $542_4$ has two or more reference colored sub sections. Thus, test sub-section $542_1$ includes reference colored sub sections $548_1$, 552 and $550_1$, test sub-section $542_2$ includes reference colored sub sections $548_2$ and $550_2$, test sub-section $542_3$ includes reference colored sub sections $548_3$ and $550_3$ and test sub-section $542_4$ includes reference colored sub sections $548_4$ and $550_4$. Insertion of liquid testing device 540 into a tested liquid will indicate according to the present embodiment whether the concentration of Cl (Free Chlorine) is within the allowable limit and thus acceptable for use or not (e.g. if the tested liquid is water, whether the water is acceptable for use).

Similarly, liquid testing device 540 is able to indicate whether the hardness of the liquid (e.g. water), the concentration of N0$_3$ (Nitrates) and Fe (Iron) are acceptable for use. Lines $556_1$, $556_2$ $556_3$ and $556_4$ indicate a limit line within test sub-sections $542_1$, $542_2$, $542_3$ and $542_4$, respectively. The limit line indicates the acceptable color limit differentiating between the acceptable and unacceptable values of concentration of reagents and substrates tested within a liquid. Thus, according to one example the hue of the test sub-sections $546_1$, $546_2$, $546_3$ and $546_4$, are compared to the reference color schemes within each of the respective test sections.

According to one example, the hue within reference colored sub section $548_4$ positioned above limit line $556_4$ indicates the unacceptable value of Iron within the tested liquid and reference colored sub section $550_4$ positioned below limit line $556_4$ indicates the acceptable value within the liquid. The color obtained in test sub-section $546_4$ after inserting liquid testing device 540 within a tested liquid is compared to reference colored sub sections $548_4$ and $550_4$. If the color within test sub-section $546_4$ is darker than reference color scheme $548_4$ the concentration of Iron is unacceptable within the tested liquid.

Similarly, if the color within test sub-section $546_4$ is lighter than reference scheme $550_4$ the concentration of Iron within the tested liquid is acceptable. According to the shown embodiment, the concentrations of Iron as represented by reference colored sub-sections $548_4$ and $550_4$ are indicated at $558_1$ and $558_2$ adjacent to the respective reference colored sub sections. Thus, if the color in test sub-section $546_4$ is identical to reference colored sub section $548_4$ or $550_4$ the user can determine the concentration of Iron within the tested liquid.

According to the present embodiment the user is able to determine whether the concentration of Iron within the tested liquid is acceptable as well as to determine the concentration of Iron within the liquid. According to other embodiments the concentration of other reagents and substrates within other test sections can be indicated beside reference color schemes.

One skilled in the art can recognize that according to other embodiments test sections for testing the concentration presence of reagents and substances can include one reference colored sub section as shown in FIG. 8A or a plurality of reference color schemes. Thus, a liquid testing device can include test sections that can include one reference colored sub section, test sections that can include two, three or any other plurality of reference color schemes for testing the concentration and presence of desired reagents and substrates within a tested liquid.

Figure 9:
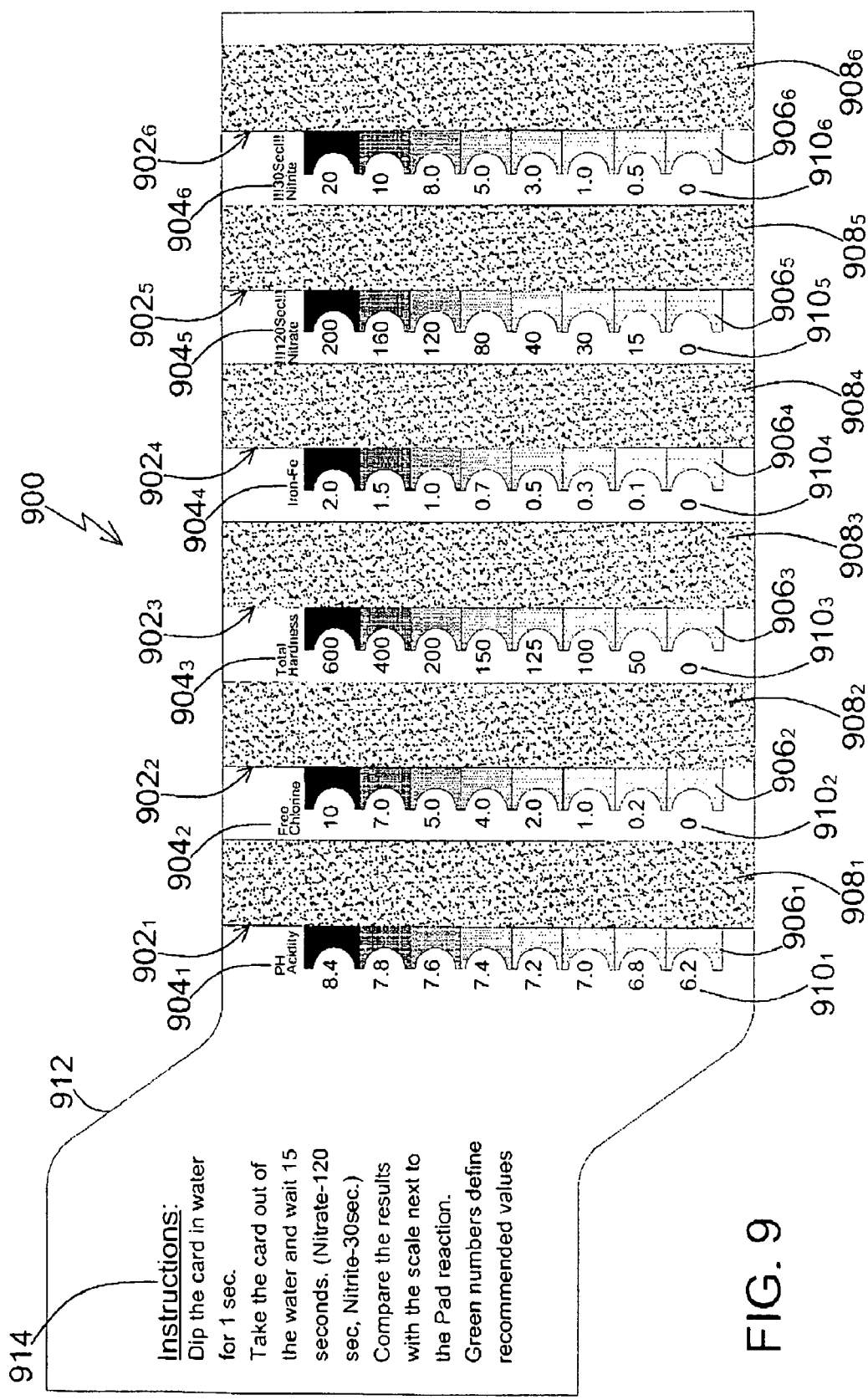
FIG. 9 illustrates the front-side of a particular liquid testing device design, constructed and operative in accordance with an embodiment of the disclosed technique.

Reference is now made to FIG. 9. FIG. 9 illustrates the front-side of a particular liquid testing device design, constructed and operative in accordance with an embodiment of the disclosed technique. As seen in the figure, liquid testing device 900 includes a plurality of test sections $902_1$, $902_2$, $902_3$, $902_4$, $902_5$ and $902_6$. Test sections $902_1$, $902_2$, $902_3$, $902_4$, $902_5$ and $902_6$ include label sections $904_1$, $904_2$, $904_3$, $904_4$, $904_5$ and $904_6$, reference color schemes $906_1$, $906_2$, $906_3$, $906_4$, $906_5$ and $906_6$, test sub-sections $908_1$, $908_2$, $908_3$, $908_4$, $908_5$ and $908_6$, and value indicating sections $910_1$, $910_2$, $910_3$, $910_4$, $910_5$ and $910_6$, respectively.

Each reference color scheme further includes a plurality of reference colored sub-sections, each of which is in a different hue. A number is printed adjacent to each reference colored sub-section in each value indicating section. As an optional feature of the present invention, the number representing the value of the test can be marked (the value can be circled), for instance, with a pen for recording the tested value.

In the particular embodiment shown in FIG. 9, test sections $902_1$, $902_2$, $902_3$, $902_4$, $902_5$ and $902_6$ are designated for testing, respectively, the pH-acidity, the concentration of free chlorine, the total hardness, and the concentrations of iron, nitrate and nitrite in water. Other test combinations, fewer or more, may be arranged as desired.

The numbers in each value indicating section represent different concentrations of the respective substance or different values of the respective parameter in the water under test. Thus, the user reads the concentration of the substance or the value of the parameter, by visual comparison of the color of a test sub-section with the respective reference scheme to determine the reference colored sub-section which matches the color of the test sub-section.

Liquid testing device 900 also includes a tab 912 to be grasped by the user when immersing liquid testing device 900 in the tested liquid. Tab 912 is designed so as to be offset from the main part of liquid testing device 900 on which the tests are conducted. Tab 912 is raised in order to allow an easy grip of liquid testing device 900. Tab 912 is provided with sufficient area to include instructions 914 for using liquid testing device 900: For the particular embodiment shown in FIG. 9, these instructions are: "Dip the card in water for 1 sec. Take card out of the water and wait 15 seconds (Nitrate=120 sec., Nitrite=30 sec). Compare the results with the scale next to the pad reaction".

It will be appreciated by persons skilled in the art that the disclosed technique is not limited to what has been particularly shown and described hereinabove. Rather, the scope of the disclosed technique is defined only by the claims which follow.

I claim:

1. An integrated, multi-test, immersable test strip-type liquid testing device for determining the value of at least one property of a liquid to be tested, the liquid testing device comprising:
   a test substrate; and
   at least one test section, located on said test substrate, including:
      a test sub-section which exhibits a reaction color according to said value, as a result of reaction of a reagent with said liquid, said reagent being impregnated within said test sub-section prior to testing; and
      a reference section located adjacent to said test sub-section, said reference section including a plurality of different reference colors and being arranged such that each of said plurality of reference colors is situated adjacent to and in contact with said test sub-section, wherein said test sub-section substantially encompasses said entire reference section having said plurality of different reference colors, such that, when said test sub-section exhibits said reaction color in accordance with a liquid property value, said value is indicated by a matching one of said reference colors which lies against said test sub-section reaction color, so as to become substantially visually merged therewith,
   said device enabling liquid analysis of the test liquid by a self-contained, one-step procedure of immersion of the entire strip including both said test sub-section and said reference section, reaction during immersion and color reading of said reaction results upon retrieval from the test liquid,
   wherein reading of said indicated value in said test sub-section is performed by visually matching said test sub-section reaction color with said substantially visually merged one of said different reference colors due to self-alignment therebetween,
   such that said indicated value of said at least one property of a liquid can be simply read in a straightforward matching process with improved accuracy in and immediate fashion,
   without requiring the physical alignment of said test sub-section reaction color with said reference colors.

2. The liquid testing device of claim 1 further comprising a plurality of test sections located on said test substrate, for simultaneously determining the value of each of a plurality of properties of a liquid to be tested,
   each of said plurality of test sections providing said reaction results,
   thereby enabling review of an entire set of said reaction results by summary inspection.

3. The liquid testing device according to claim 1, wherein said indicated value is provided in a recordable form.

4. The liquid testing device of claim 1, wherein said test section further comprises a label respective of a property of said liquid.

5. The liquid testing device of claim 2, wherein each of said properties is a concentration of a different substance in said liquid.

6. The liquid testing device of claim 5, wherein said different substance can be:
aluminum;
alkalinity;
ammonia;
arsenic;
silver;
ascorbic acid;
bromine;
calcium;
carbonate;
chloride;
cobalt;
cyanide;
fluoride;
formaldehyde;
glycol;
iodine;
manganese;
molybdenum;
nickel;
mercury;
metals;
hardness;
peraceric acid;
peroxide;
chromium;
phosphate;
potassium;
sulfate;
sulfite;
tin;
permanganate;
pesticide;
protein;
glucose;
ketones;
urobilinogen;
bilirubin;
leucocytes;
chlorochromate;
oxidants;
ammonium;
pyridinium;
creatinine;
glutaraldehyde;
salt;
specific gravity;
nitrate;
nitrite;
lead;
chromat;
zinc;
*escherichia Coli;*
sodium;
iron;
copper;
pH;
acidity;
chlorine;
cyanuric acid;
bacteria;
sedimentation;
hydrogen sulfide; and
the like.

7. The liquid testing device of claim 1, wherein said device is capable of testing liquids such as:
water;
water solutions;
liquid fuel;
crude oil;
body liquids and blood components;
food and beverages;
urine; and
the like.

8. The liquid testing device of claim 1, wherein said test substrate is made of a material selected from the list consisting of:
flexible polymer;
rigid polymer;
fabricated materials;
glass;
paper;
plastic coated paper;
cardboard;
timber;
dry clay;
ceramic;
masonry;
leather;
textile; and
metal.

9. The liquid testing device of claim 1, wherein said test substrate is in the form of a sheet.

10. The liquid testing device of claim 9, wherein the geometry of said sheet is selected from the list consisting of:
rectangle;
square;
triangle;
rhombus;
parallelogram;
trapezoid;
quadrilateral;
circle;
annulus;
ellipse;
sector of a circle; and
freeform closed curve.

11. The liquid testing device of claim 9, wherein the form of said sheet is selected from the list consisting of:
flat;
rolled;
folded;
twisted;
convex; and
concave.

12. The liquid testing device of claim 1, wherein said different reference colors are of the same hue, and wherein each of said reference colors are of different saturation levels and different brightness levels.

13. The liquid testing device of claim 1, wherein at least one of said different reference colors designating an acceptable value of a property of said liquid, is separated by a limit line, from at least another one of said different reference colors designating an unacceptable value of said property.

14. The liquid testing device of claim 1, wherein said test section further comprises a value indicating section, said value indicating section includes a plurality of numbers, each of said numbers is located adjacent to a respective reference color, each of said numbers represents a selected value of a property of said liquid.

15. The liquid testing device of claim 14, wherein a selected one of said numbers is represented in a different style, thereby separating at least one number which designates an acceptable value of said property, from at least another number which designates an unacceptable value of said property.

16. The liquid testing device of claim 15, wherein said different style is selected from the list consisting of:
   bold;
   italics;
   underlined;
   color;
   font; and
   size.

17. The liquid testing device of claim 2 further comprising:
   a container, having at least a transparent portion, within which said test substrate is disposed.

18. The liquid testing device of claim 17, further comprising a stopper for closing an at least partially open end of said container.

19. The liquid testing device of claim 17, wherein said container is made of a material selected from the list consisting of:
   polymer;
   glass;
   timber;
   dry clay;
   ceramic;
   masonry; and
   metal.

20. The liquid testing device of claim 17, wherein the cross section of said container is selected from the list consisting of:
   rectangle;
   square;
   triangle;
   rhombus;
   parallelogram;
   trapezoid;
   quadrilateral;
   circle;
   annulus;
   ellipse;
   sector of a circle; and
   freeform closed curve.

21. The liquid testing device of claim 17, wherein said container comprises a plurality of different labels respective of different ones of said properties, each of said different labels being located adjacent to a respective one of said test sections.

22. The liquid testing device of claim 17, wherein each one of said test sections is attached to the inner wall of said container.

23. The liquid testing device of claim 17, wherein said test section is replaced by an unused test section of the same kind, after testing said liquid.

24. The liquid testing device of claim 17, wherein a reference section respective of a property of said liquid is in form of a circle, said different reference colors respective of said reference section are in form of sectors of said circle and a test section respective of said property, is in form of an annulus surrounding said circle.

25. The liquid testing device of claim 17 further comprising:
   a plurality of containers, each container having,
      at least a transparent portion; and
      a test substrate disposed therein.

26. The liquid testing device of claim 25, wherein said containers are part of a solid body.

27. The liquid testing device of claim 25, wherein each of said containers is a separate body, and wherein said containers are attached together by an adhesive or at least one fastener or welding.

28. The liquid testing device of claim 25, further comprising an at least partially open end of each of said containers and a stopper for closing an at least partially open end of each of said containers.

29. The liquid testing device of claim 27, further comprising a plurality of stoppers, wherein said stoppers are part of a body.

30. The liquid testing device of claim 25, wherein said containers are constructed as separate cavities within a single body.

31. A method for determining the value of at least one property of a liquid to be tested, the method comprising the steps of:
   providing at least one test section on a test substrate;
   pre-associating a multiple color reference scheme with a property test substance which has been impregnated within said at least one test section prior to testing, such that the reference color of said reference scheme is situated adjacent to and in contact with said property test substance on said test section, wherein said test section substantially encompasses said entire reference scheme having said multiple reference colors;
   immersing said test substrate in said liquid, the property test substance on said at least one test section exhibiting, in accordance with a value of said liquid property, a test reaction color that matches one of the reference colors located on its adjacent reference scheme, so as to become substantially visually merged therewith;
   identifying said exhibited test reaction color of said property test substance that matches a selected one of different reference colors of said multiple color reference scheme, without requiring the physical alignment of said test sub-section with said reference colors; and
   determining a respective one of said values according to the outcome of said identifying step, by visually matching said exhibited test reaction color with one of said different reference colors due to self-alignment therebetween.

32. The method of claim 31, wherein said determining step further comprises reading a selected one of a plurality of numbers, said selected number designating said value, and
   wherein each of said numbers is located adjacent to a respective one of said different colors.

33. The method of claim 31 further comprising:
   providing a plurality of test sections located on said test substrate, for simultaneously determining the value of each of a plurality of properties of a liquid to be tested,
   each of said plurality of test sections providing said reaction results,
   thereby enabling review of an entire set of said reaction results by summary inspection.

34. The method of claim 33, wherein said determined respective one of said values is provided in a recordable form.

* * * * *